US006482848B2

(12) United States Patent
Moon et al.

(10) Patent No.: US 6,482,848 B2
(45) Date of Patent: Nov. 19, 2002

(54) PRODRUGS OF 3-(PYRROL-2-YLMETHYLIDENE)-2-INDOLINONE DERIVATIVES

(75) Inventors: Malcolm Wilson Moon, Kalamazoo, MI (US); Walter Morozowich, Kalamazoo, MI (US); Ping Gao, Portage, MI (US); Marcel Koenig, Burlingame, CA (US)

(73) Assignee: Sugen Incorporated, South San Francisco, CA (US)

( * ) Notice: Subject to any disclaimer, the term of this patent is extended or adjusted under 35 U.S.C. 154(b) by 0 days.

(21) Appl. No.: 09/863,819

(22) Filed: May 24, 2001

(65) Prior Publication Data

US 2002/0037878 A1 Mar. 28, 2002

Related U.S. Application Data

(60) Provisional application No. 60/207,000, filed on May 24, 2000, and provisional application No. 60/225,045, filed on Aug. 11, 2000.

(51) Int. Cl.$^7$ .................. C07D 209/10; A61K 31/404; A61P 17/02
(52) U.S. Cl. .................. 514/418; 548/467; 548/468; 548/486
(58) Field of Search .................. 548/467, 468, 548/486; 514/418

(56) References Cited

U.S. PATENT DOCUMENTS

| 2,968,557 | A | 1/1961 | Burgandt et al. | |
|---|---|---|---|---|
| 4,002,749 | A | 1/1977 | Rovnyak | |
| 4,053,613 | A | 10/1977 | Rovnyak et al. | |
| 4,420,639 | A | 12/1983 | Lake et al. | 568/328 |
| 4,472,382 | A | 9/1984 | Labrie et al | 424/177 |
| 4,636,505 | A | 1/1987 | Tucker | 514/256 |
| 4,642,309 | A | 2/1987 | Michel et al. | |
| 4,826,847 | A | 5/1989 | Michel et al. | |
| 5,051,417 | A | 9/1991 | Nadler et al. | |
| 5,124,347 | A | 6/1992 | Connor et al. | |
| 5,196,446 | A | 3/1993 | Levitzki et al. | |
| 5,302,606 | A | 4/1994 | Spada et al. | |
| 5,322,950 | A | 6/1994 | Sircar et al. | |
| 5,374,652 | A | 12/1994 | Buzzetti et al. | |
| 5,382,593 | A | 1/1995 | Le Baut et al. | |
| 5,389,613 | A | 2/1995 | Labrie et al. | 514/15 |
| 5,389,661 | A | 2/1995 | Sircar et al. | |
| 5,397,787 | A | 3/1995 | Buzzetti et al. | |
| 5,409,949 | A | 4/1995 | Buzzetti et al. | |
| 5,777,134 | A | 7/1998 | Bakshi et al. | 549/276 |
| 5,792,783 | A | 8/1998 | Tang et al. | |
| 5,834,504 | A | 11/1998 | Tang et al. | |
| 5,849,710 | A | 12/1998 | Battistini et al. | |
| 5,880,141 | A | 3/1999 | Tang et al. | |
| 5,883,113 | A | 3/1999 | Tang et al. | |
| 5,883,116 | A | 3/1999 | Tang et al. | |
| 5,886,020 | A | 3/1999 | Tang et al. | |
| 5,985,868 | A | 11/1999 | Gray | 514/220 |
| 5,994,362 | A | 11/1999 | Gormley et al. | 514/284 |
| 6,133,305 | A | 10/2000 | Tang et al. | |

FOREIGN PATENT DOCUMENTS

| AU | 286870 | 5/1967 | |
|---|---|---|---|
| CA | 2012634 | 9/1991 | |
| DE | 2159360 | 11/1971 | |
| DE | 2159361 | 11/1971 | |
| DE | 2159362 | 11/1971 | |
| DE | 2159363 | 11/1971 | |
| DE | 2321656 | 4/1973 | |
| DE | 3426419 | 1/1986 | |
| EP | 0351213 | 1/1990 | |
| EP | 0252713 | 9/1990 | |
| EP | 0525472 | 2/1993 | |
| EP | 0632102 | 1/1995 | |
| EP | 0662473 | 7/1995 | |
| EP | 0769947 | 5/1997 | |
| EP | 0788890 | 8/1997 | |
| EP | 0934931 | 8/1999 | |
| EP | 1082305 A1 | 3/2001 | |
| FR | 1398224 | 3/1965 | |
| FR | 1599772 | 8/1970 | |
| FR | 2689397 | 10/1993 | |
| GB | 809691 | 3/1959 | |
| GB | 835473 | 5/1960 | |
| JP | 6239564 | 2/1987 | |
| JP | 6229570 | 7/1987 | |
| JP | 63141955 | 6/1988 | |
| JP | 558894 | 3/1993 | |
| WO | 91/13055 | 9/1991 | |
| WO | 92/07830 | 5/1992 | |
| WO | 92/20642 | 11/1992 | |
| WO | 93/01182 | 1/1993 | |
| WO | WO94/08986 | 4/1994 | C07D/311/22 |
| WO | 94/14808 | 7/1994 | |
| WO | 95/01349 | 1/1995 | |
| WO | 95/17181 | 6/1995 | |
| WO | WO95/19770 | 7/1995 | A61K/31/275 |
| WO | 96/22976 | 8/1995 | |
| WO | 96/00226 | 1/1996 | |
| WO | 96/16964 | 6/1996 | |

(List continued on next page.)

OTHER PUBLICATIONS

Andreani et al., "Potential Antitumor Agents. 25[1]. Synthesis and Cytotoxic Activity of 3-(2-Chloro-3-Indolymethylene)1,3-Dihydroindol-2-Ones," *Anticancer Research* 16:3585-3588 (1996)©Elsevier, Paris.

(List continued on next page.)

Primary Examiner—Joseph K. McKane
Assistant Examiner—Kamal Saeed
(74) Attorney, Agent, or Firm—Foley & Lardner

(57) ABSTRACT

The present invention is directed to prodrugs of certain 3-(pyrrol-2-yl-methylidene)-2-indolinone derivatives that modulate the activity of protein kinases ("PKs"). Pharmaceutical compositions comprising these compounds, methods of treating diseases related to abnormal PK activity utilizing pharmaceutical compositions comprising these compounds and methods of preparing them are also disclosed.

19 Claims, No Drawings

FOREIGN PATENT DOCUMENTS

| WO | 96/32380 | 10/1996 | |
|---|---|---|---|
| WO | 96/40116 | 12/1996 | |
| WO | 97/25986 | 7/1997 | |
| WO | 98/07695 | 2/1998 | |
| WO | 98/38984 | 4/1998 | |
| WO | 98/24432 | 6/1998 | |
| WO | 98/50356 | 11/1998 | |
| WO | WO98/55153 | 12/1998 | .......... A61K/49/04 |
| WO | 99/10325 | 3/1999 | |
| WO | 99/52869 | 10/1999 | |
| WO | 99/61422 | 12/1999 | |
| WO | 99/65869 | 12/1999 | |
| WO | 00/08202 | 2/2000 | |
| WO | 00/35906 | 6/2000 | |
| WO | 00/35908 | 6/2000 | |
| WO | 00/35909 | 6/2000 | |
| WO | 00/38519 | 7/2000 | |
| WO | 00/56709 | 9/2000 | |
| WO | 01/60814 | 8/2001 | |

OTHER PUBLICATIONS

Andreani et al., "Synthesis and cardiotonic activity of 2–indolinones," *Eur. J. Med. Chem.* 25:187–190 (1990).

Andreani et al., "Synthesis and cardiotonic activity of 2–indolinones bearing pyridyl groups," *Eur. J. Med. Chem.* 28:653–657 (1993)©Elsevier, Paris.

Andreani et al., "Synthesis and cariotonic activity of pyridylmethylene–2–indolinones," *Eur. J. Med. Chem.* 27:167–170 (1992)©Elsevier, Paris.

Andreani et al., "Synthesis and potential coanthracyclinic activity of substituted 3–(5–imidazo[2,1–b]thiazolylmethylene)–2–indolinones," *Eur. J. Med. Chem.* 32:919–924 (1997)©Elsevier, Paris.

Andreani et al., "Synthesis of lactams with potential cardiotonic activity," *Eur. J. Med. Chem.* 28:825–829 (1993).

Andreani et al., "In Vivo Cardiotonic Activity of Pyridylmethylene–2–indolinones," *Arzneimittel–Forschung Drug Research* 48:727–729 (1998)©.

Bahner and Brotherton, "9–(4–Aminobenzylidene)fluorenes," *J. Med. Chem.* 12:722–723 (1969).

Bahner et al., "Benzylideneindenes with Oxygen Attached to the Indene Ring," *J. Med. Chem.* 12:721–722 (1969).

Bamfield et al., "Diels–Alder Reactions of Oxindolylideneacetone," *J. Chem. Soc. (C)* 1028–1030 (1996)©.

Borsche et al., "Über vielkernige kondensierte Systeme mit heterocyclischen Ringen. XIII.," *Liebigs Ann. Chem.* 550:160–174 (1941).

Buzzetti et al., "Cinnamamide Analogs as Inhibitors of Protein Tyrosine Kinases," *II Farmaco* 48:615–636 (1993).

Chatten et al., "Substituted Oxindoles. Part VI. Polarographic Reduction of Substituted trans–3–Benzylideneindol–2(3H)–ones," *J. Chem. Soc. Perkin II:* 469–473 (1973).

Coda et al., "(Z)– and (E)–Arylidene–1, 3–dihydroindol–2–ones: Configuration, Conformation and Infrared Carbonyl Stretching Frequencies," *J. Chem. Soc. Perkin Trans. II:* 615–619 (1984).

Coda et al., "3–(4–methylbenzilidene)–1, 3–dihydroindol–2–one," *Journal of the Chemical Society, Perkin Transactions 2* 4:615–620 (1984) Database Crossfire, Beilstein Reference No. 6–21.

Decodts et al., "Suicide inhibitors of proteases. Lack of activity of halomethyl derivatives of some aromatic lactams," *Eur. J. Med. Chem* 18: 107–111 (1983).

Desimoni et al., "Catalysis with Inorganic Cations. $V^1$ Intramolecular Hetero Diels–Alder versus Ene Reactions: Effect of Magnesium perchlorate on Chemoselectivity," *Tetrahedron* 52(36) 12009–12018 (1196) ©Pergamon.

Elliott and Rivers, "Reduction of Some Oxindolylidene Derivatives to 3–Substituted Oxindoles by Sodium Borohydride," *J. Med. Chem.* 29:2438–2440 (1964).

Elliott et al., "1–methyl–2–(3–oxindolidenmethyl)–pyridinium," *Journal of Organic Chemistry* 29:2438–2440 (1964) Database Crossfire, Beilstein Reference No. 5–24.

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991) copyright Am. Clem. Soc.

Hirao et al., "Rhodium–Catalyzed Carbonylation of 2–Alkynylaniline: Syntheses of 1,3–Dihydroindol–2–ones," *Tetrahedron Letters* 36(35) 1995©Pergamon.

Hodges et al., "Chemical and biological properties of some oxindolidyl–3–methines," *Canadian J. Chemistry* 46:2189–2194 (1968).

Howard, Harry R., "Lactam Derivatives," U.S. Provisional Patent Application No. 60/015134.

Howard et al., "Synthesis and aldose reductase inhibitory activity of substituted 2(1H)–benzimidazolone– and oxindole–1–acetic acids," *Eur. J. Med. Chem.* 27:779–789 (1992)©Elsevier, Paris.

Katritzky et al., "Color and Constitution. Part 8[1]. Some Novel Dyestuffs Containing Indoxyl Residues," *J. Heterocyclic Chem.* 25:1287–1292 (1988).

Kobayashi et al., "Anti–tumor Activity of Indole Derivatives," *Yakugaku Zasshi* 97:1033–1039 (1977).

Kovac and Stetinova, "Furan derivatives. LXXX. Synthesis and properties of substituted furfurylidenoxindoles," *Chem. rvesu* 30:484–492 (1976).

Levitzki and Gazit, "Tyrosine Kinase Inhibition: An Approach to Drug Development," *Science* 267:1782–1788 (1995).

Mariani et al., "Inhibition of angiogenesis by FCE 26806, a potent tyrosine kinase inhibitor," *Experimental Therapeutics—Proceedings of the American Association for Cancer Research* 35:381 at abstract No. 2268 (Mar. 1994).

Mohammadi et al., "Structures of the Tyrosine Kinase Domain of Fibroblast Growth Factor Receptor in Complex with Inhibitors," *Science* 276:955–960 (1997)©American Association for the Advancement of Science.

Neber and Röcker, "On the action of benzaldehydes on the free o–aminophenylacetic acid (II)," *Chem. Ber.* 56:1710–1716 (1923) (German and English Translation).

Nodiff et al., "Antimalarial Phenanthrene Amino Alchohols. 3. Halogen–containing 9–phenanthrenemethanols," *Chemical Abstracts,* vol. 83, abstract No. 188214 (1975).

O'Sullivan and Rothery, "The Preparation and Possible Clinical Significance of 4'–Dialkylaminoisoindogenides," *Clinica Chimica Acta* 62:181–182 (1975) ©Elsevier Scientific Publishing Company.

Pavlenko et al., "Introduction of aminomethyl groups into heterocyclic CH–acid molecules," *Dopov. Akad. Nauk Ukr Rsrs, Ser. B: Geol., Khim. Biol. Nauki* 7:64–66 (1980.

Plowman et al., "Receptor Tyrosine Kinases as Targets for Drug Intervention," *DN&P* 7:334–339 (1994).

Quallich et al., A General Oxindole Synthesis, *J. Synthetic Organic Chemistry:* 51–51 (1993).

Schuchter et al., "Successful Treatment of Murine Melanoma with Bryostatin 1," *Cancer Research* 51:682–687 (1991).

Shiraishi et al., "Specific inhibitors of Tyrosine–Specific Protein Kinase, Synthetic 4–Hydroxycinnamamide Derivatives," *Biochemical and Biophysical Research Communications* 147:322–328 (1987)©Academic Press.

Shiraishi et al., "Specific Inhibitors of Tyrosine–specific Protein Kinases: Properties of 4–Hydroxycinnamamide Derivatives in Vitro," *Cancer Research* 49:2374–2378 (1989).

Singh et al., "Indolinone Derivatives as Potential Antimicrobial Agents," *Zentralbl. Mikrobiol.* 144:105–109 (1989) copyright VEG Gustav Fischer Verlag Jena.

Spada, et al., "Small molecule inhibitors of tyrosine kinase activity," *Expert Opinion on Therapeutic Patents* 5:805–817 (1995) ©Ashley Publications.

Sun et al., "Design, Synthesis, and Evaluations of Substituted 3–[(3– or 4–Carboxyethylpyrrol–2–yl) methylidenyl] indolin–2–ones as Inhibitors of VEGF, FGF, and PDGF Receptor Tyrosine Kinases," *Journal of Medicinal Chemistry* 42: 5120–5130 (1999) ©American Chemical Society.

Sun et al, "Synthesis and Biological Evaluations of 3–Substituted Indolin–2–ones: A Novel Class of Tyrosine Kinase Inhibitors That Exhibit Selectivity toward Particular Receptor Tyrosine Kinases," *J. Med. Chem.* 41:2588–2603 (1988)©The American Chemical Society.

Tacconi and Marinone, "Preparazione e caratteristiche di alcuni 3–ossindolidenderivati," *Ricerca Scientifica* 38:1239–1244 (1968).

Tacconi et al., "(Z)– and (E)–3–Alkylidene–1, 3–dihydroindol–2–ones: Influence of Configuration on the Transmission of the Inductive Effect to the Carbonyl Group," *J.C.S. Perkin II* 150–154 (1976).

Thompson et al., "Facile Dimerisation of 3–Benzylideneindoline–2–thiones," *J. Chem. Soc. Perkin Trans. (I)* 1835–1837 (1993).

Traxler, "Protein tyrosine kinase inhibitors in cancer treatment," *Expert Opinion on Therapeutic Patents* 7(6):571–588 (1997)©Ashley Publications Ltd.

Wahl et al., "3–benzilidene–5–methyl–1, 3–dihydroindol–2–one," *Ann. Chim.* 350 (1926), Database Crossfier, Beilstein Reference No. 2–21–00–00290.

Wahl, Beilstein Reg. No. 191439, *Bull Soc. Chim. Fr.,* p. 1038 (1909).

Wahl, Beilstein Reg. No. 231732, *Bull. Soc. Chim. Fr.,* pp. 1035–1038 (1909).

Walker et al., "Synthesis of New 3–(Pyridylmethylene)–, 3–(Pyridylmethyl)–, 3–(Piperdylmethyl)–, and 3–(β–Alkylaminoethyl)–2–indolinones. The Reduction of Isoindogenides, Nitro Compounds, and Pyridines in a Series of 2–Indolinones," *J. Med. Chem.* 8:626–637 (1965).

Wright et al., "Cyclic Hydroxamic Acids Derived from Indole," *J. Am. Chem. Soc.* 78:221–224 (1956).

Wright et al., "Inhibition of Angiogenesis in Vitro and In Ovo With an Inhibitor of Cellular Protein Kinases, MDL 27032," *J. Cellular Physiology* 152:448–457 (1992).

Zhang et al., "Microtubule Effects of Welwistatin, a Cyanobacterial Indolinone that Circumvents Multiple Drug Resistance," *Molecular Pharmacology* 49:228–234 (1996) copyright The American Society for Pharmacology and Experimental Pharmaceutics.

Zhungietu et al., "Reaction of Indoles and 2–Ketoindolines With Some Aldehydes," *Chemical Abstracts,* vol. 78, abstract No. 111201 (1990).

English Translation of Hungarian Patent No. 3899/92.

English Translation of German Patent No. 2159360 (Ref. No. A85).

English Translation of German Patent No. 2159361 (Ref. No. A86).

English Translation of German Patent No. 2159363 (Ref. No. A88).

English Translation of German Patent No. 2321656 (Ref. No. A89).

English Translation of German Patent No. 3426419 (Ref. No. A90).

English Translation of European Patent No. 580502 (Ref. No. A96).

English Translation of European Patent No. 632102 (Ref. No. A98).

English Translation of French Patent No. 2689397 (Ref. No. A107).

English Translation of Japanese Patent No. 6229570 (Ref. No. A110).

English Translation of Japanese Patent No. 6239564 (Ref. No. A111).

English Translation of Japanese Patent No. 63141955 (Ref. No. A 112).

English Translation of Japanese Patent No. 558894 (Ref. No. A113).

English Translation of German Patent No. 878539 (Ref. No. A84).

English Translation of French Patent No. 1398224 (Ref. No. A105).

English Translation of French Patent No. 15997722 (Ref. No. A106).

Tucker et al., "Resolution of the Nonsteroidal Antiandrogen 4'–Cyano–3–[(4–fluorophenyl)sulfonyl] –2–hydroxy–2–methyl–3'–(trifluoromethyl)–propionanilide and the Determination of the Absolute Configuration of the Active Enantiomer", *J. Med. Chem.,* 31(4) 885–887 (1988).

International Search Report corresponding to International Application No. PCT/US00/41609; mailed Apr. 12, 2110.

Tucker et al., "Nonsteroidal Antiandrogens. Synthesis and Structure–Activity Relationships of 3–Substituted Derivatives of 2–Hydroxypropionanilides," *J. Med. Chem.,* 31(5) 954–959 (1988).

Casodex (bicalutamide, 50 mg tablets) Professional Information Brochure, <http://www.astrazenecaus.com/pi/pib_casodex.htm>, pp. 1–9, Jun. 26, 2000.

PRODRUGS OF 3-(PYRROL-2-YLMETHYLIDENE)-2-INDOLINONE DERIVATIVES

CROSS-REFERENCE

This application claims priority under 35 U.S.C. 119(e) to U.S. Provisional applications Serial No. 60/207,000 filed on May 24, 2000, and No. 60/225,045, filed on Aug. 11, 2000, the disclosures of which are incorporated herein by reference in their entirety.

BACKGROUND OF THE INVENTION

1. Field of Invention

The present invention is directed to prodrugs of certain 3-(pyrrol-2-ylmethylidene)-2-indolinone derivatives that modulate the activity of protein kinases ("PKs"). Pharmaceutical compositions comprising these compounds, methods of treating diseases related to abnormal PK activity utilizing pharmaceutical compositions comprising these compounds and methods of preparing them are also disclosed.

2. State of the Art

Protein kinases ("PKs") are enzymes that catalyze the phosphorylation of hydroxy groups on tyrosine, serine and threonine residues of proteins. PKs can be conveniently broken down into two classes, the protein tyrosine kinases (PTKs) and the serine-threonine kinases (STKs). One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc (See., Schlessinger and Ullrich (1992) Neuron 9:303–391).

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. Another group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1–4, and seven ligands, FGF1–7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A more complete listing of the known RTK subfamilies is described in Plowman et al., DN&P, 7(6):334–339 (1994) which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, Oncogene, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. For example, attempts have been made to identify small molecules which act as PK inhibitors. For example, bismonocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660), and benzylphosphonic acid compounds (PCT WO 91/15495). Additionally, a family of novel pyrrole-substituted 2-indolinone compounds have been discovered which exhibit PK modulating ability and have a salutary effect against disorders related to abnormal PK activity (U.S. Pat. No. 5,792,783 and PCT Application Publication No. WO 99/61422). Administration of various species of pyrrole-substituted 2-indolinone compounds has been shown to be an effective therapeutic approach to cure many kinds of solid tumors. For example, 3-(3,5-dimethyl-1H-pyrrol-2-ylmethylidene)-1,3-dihydro-indol-2-one, a highly active selective inhibitor of the vascular endothelial growth factor receptor (Flk-1/KDR), inhibits tyrosine kinase catalysis, tumor vascularization, and growth of multiple tumor types (Fong et al. (1999) *Cancer Res.* 59:99–106). These compounds, however, have high lipophilicity and low solubility in water and most common vehicles at physiological pH limit their adminstration.

Accordingly, there is a need for PK inhibitors that do not exhibit such drawbacks. The present invention fulfills this and related needs.

SUMMARY OF THE INVENTION

In one aspect, this invention relates to compounds having the formula I, II, III, or IV:

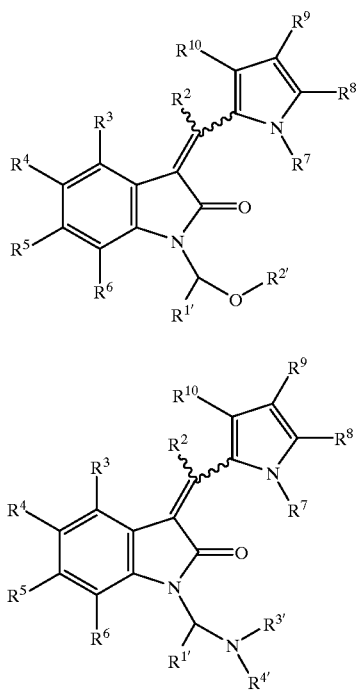

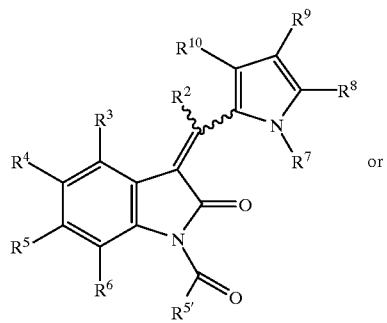

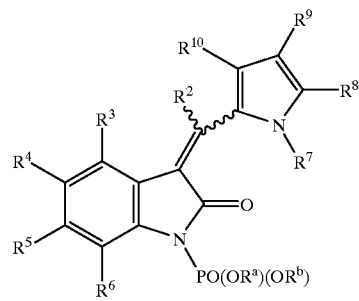

wherein:
$R^2$ is hydrogen;
$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbarnyl, amino and —$NR^{11}R^{12}$ where $R^{11}$ and $R^{12}$ are independently selected from the group consisting of hydrogen, alkyl, cycloalkyl, aryl, carbonyl, acetyl, sulfonyl, and trifluoromethanesulfonyl, or $R^{11}$ and $R^{12}$, together with the nitrogen atom to which they are attached, combine to form a five- or six-member heteroalicyclic ring provided that at least two of $R^3$, $R^4$, $R^5$ and $R^6$ are hydrogen; or
$R^3$ and $R^4$, $R^4$ and $R^5$, or $R^5$ and $R^6$ combine to form a six-membered aryl ring, a methylenedioxy or an ethylenedioxy group;
$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethanesulfonyl;
$R^8$, $R^9$ and $R^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —NR$^{11}$R$^{12}$ wherein R$^{11}$ and R$^{12}$ are as defined above;

R$^{1'}$ is hydrogen or alkyl;

R$^{2'}$ is hydrogen, alkyl, aralkyl, acyl, or —P(O)(OR)(OR');

R$^{3'}$ and R$^{4'}$ are independently alkyl, or R$^{3'}$ and R$^{4'}$, together with the nitrogen atom to which they are attached, combine to form a heteroalicyclic ring or a heteroaryl ring provided that the heteroalicyclic ring is not piperidin-1-yl or morpholin-4-yl;

R$^{5'}$ is alkyl;

R and R' are independently selected from the group consisting of hydrogen, alkyl, aralkyl and aryl; and R$^a$ and R$^b$ are independently selected from hydrogen or alkyl; or a pharmaceutically acceptable salt thereof.

Preferably, the invention is directed to a compound having the formula I, III, or IV:

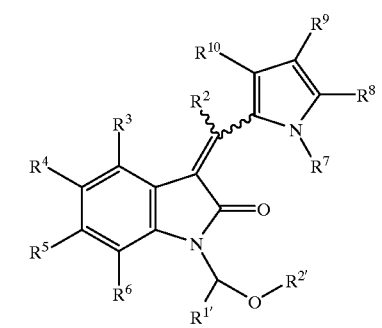

I

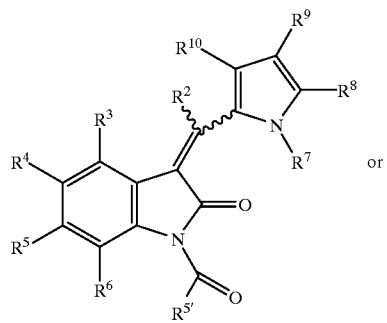

III

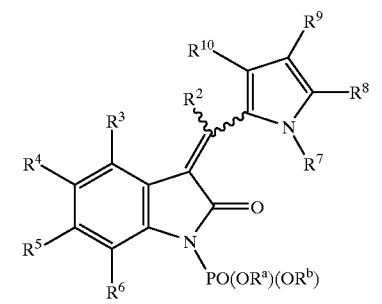

IV wherein:

R$^2$ is hydrogen;

R$^3$, R$^4$, R$^5$ and R$^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$ where R$^{11}$ and R$^{12}$ are independently selected from the group consisting of hydrogen, alkyl, cycloalkyl, aryl, carbonyl, acetyl, sulfonyl, and trifluoromethanesulfonyl, or R$^{11}$ and R$^{12}$, together with the nitrogen atom to which they are attached, combine to form a five- or six-membered heteroalicyclic ring provided that at least two of R$^3$, R$^4$, R$^5$ and R$^6$ are hydrogen; or R$^3$ and R$^4$, R$^4$ and R$^5$, or R$^5$ and R$^6$ combine to form a six-membered aryl ring, a methylenedioxy or an ethylenedioxy group;

R$^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethanesulfonyl;

R$^8$, R$^9$ and R$^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —NR$^{11}$R$^{12}$ wherein R$^{11}$ and R$^{12}$ are as defined above;

R$^{1'}$ is hydrogen or alkyl;

R$^{2'}$ is hydrogen, alkyl, aralkyl, acyl, or —P(O)(OR)(OR');

R$^{5'}$ is alkyl;

R and R' are independently selected from the group consisting of hydrogen, alkyl, aralkyl and aryl;

R$^a$ and R$^b$ are independently selected from hydrogen or alkyl; or a pharmaceutically acceptable salt thereof.

Specifically, the compounds of the present invention convert in vivo to compounds of Formula V:

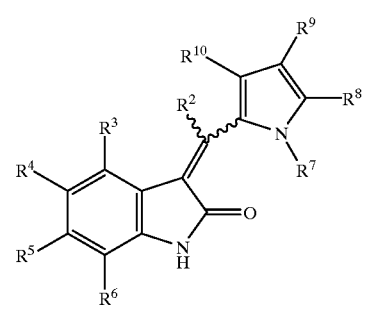

V that exhibit PK modulating ability, in particular PK inhibiting ability, and are therefore useful in treating disorders related to abnormal PK activity. The active compound (V) formed from the compounds of the present invention are described in U.S. Pat. No. 5,792,783, PCT Application Publication No. WO 99/61422, and U.S. patent application Ser. No. 09/783,264, filed on Feb. 15, 2001, and titled "PYRROLE SUBSTITUTED 2-INDOLINONE AS PRO- TEIN KINASE INHIBITORS", the disclosures of which are hereby incorporated by reference. The prodrug compounds of the present invention have advantages over compounds of Formula (V) by virtue of unexpected increased aqueous solubility over the parent compound thus making them particularly suitable for intravenous (IV) formulations. A general description of the advantages and uses of prodrugs as pharmaceutically useful compounds is given in an article by Waller and George in *Br. J. Clin. Pharmac.*, Vol. 28, pp. 497–507, 1989.

In a second aspect this invention is directed to a pharmaceutical composition comprising one or more compound(s) of Formula I–IV, preferably, I, III, or IV or a pharmaceutically acceptable salt thereof and a pharmaceutically acceptable excipient.

In a third aspect, this invention is directed to a method of treating diseases mediated by abnormal protein kinase activity, in particular, receptor tyrosine kinases (RTKs), non-receptor protein tyrosine kinases (CTKs) and serine/threonine protein kinases (STKs), in an organism, in particular humans, which method comprises administering to said organism a pharmaceutical composition comprising a compound of Formula Formula I–IV, preferably, I, III, or IV, or a pharmaceutically acceptable salt thereof and a pharmaceutically acceptable excipient. Such diseases include by way of example and not limitation, cancer, diabetes, hepatic cirrhosis, cardiovascular disease such as atherosclerosis, angiogenesis, immunological disease such as autoimmune disease (e.g., AIDS and lupus) and renal disease. Specifically, the diseases mediated by EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R, FGFR-4R, Src, Frk, Btk, Csk, Abl, ZAP70, Fes/Fps, Fak, Jak, Ack, Yes, Fyn, Lyn, Lck, Blk, Hck, Fgr, Yrk, CDK2 and Raf.

In a fourth aspect, this invention is directed to a method of modulating the catalytic activity (e.g., inhibiting the catalytic activity) of PKs, in particular receptor tyrosine kinases (RTKs), non-receptor protein tyrosine kinases (CTKs) and serine/threonine protein kinases (STKs), using a compound of this invention or a pharmaceutical composition comprising a compound of this invention and a pharmaceutically acceptable excipient. The method may be carried out in vitro or in vivo. In particular, the receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R. The cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. The serine-threonine protein kinase whose catalytic activity is modulated by a compound of this invention is selected from the group consisting of CDK2 and Raf.

In a fifth aspect, this invention is directed to the use of a compound of formula Formula I–IV, preferably, I, III, or IV in the preparation of a medicament useful in the treatment of a disease mediated by abnormal PK activity.

In a sixth aspect, this invention is directed to a method of preparing a compound of formula II which method comprises reacting a compound of Formula V

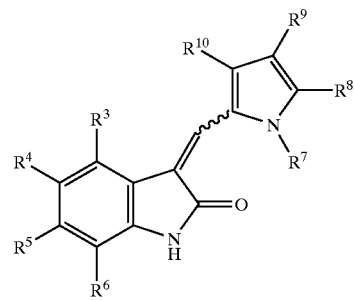

with an amine of formula —$NR^{3'}R^{4'}$ in the presence of an aldehyde of formula $R^{1'}CHO$ where $R^{1'}$, $R^{3'}$ and $R^{4'}$ are as defined in formula II above;

optionally modifying any of the $R^3$–$R^{10}$ groups; and optionally preparing an acid addition salt thereof.

DETAILED DESCRIPTION OF THE INVENTION

Definitions

Unless otherwise stated the following terms used in the specification and claims have the meanings discussed below:

"Alkyl" refers to a saturated aliphatic hydrocarbon including straight chain, or branched chain groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms e.g., methyl, ethyl, n-propyl, isopropyl, butyl, iso-butyl, tert-butyl and the like. The alkyl group may be substituted or unsubstituted. When substituted, the substituent group(s) is preferably one or more, more preferably one or two groups, individually selected from the group consisting of cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino, ammonium and —$NR^{13}R^{14}$ where $R^{13}$ and $R^{14}$ are independently selected from the group consisting of hydrogen, unsubstituted alkyl, alkyl, cycloalkyl, aryl, carbonyl, acetyl, sulfonyl, amino, and trifluoromethanesulfonyl, or $R^{13}$ and $R^{14}$, together with the nitrogen atom to which they are attached, combine to form a five- or six-member heteroalicyclic ring. More preferably, the substituent is hydroxy, amino, or —$NR^{13}R^{14}$ where $R^{13}$ and $R^{14}$ are independently selected from the group consisting of unsubstituted alkyl, alkyl substituted with amino or hydroxy, or $R^{13}$ and $R^{14}$ together with the nitrogen atom to which they are attached combine to form pyrrolidine, morpholine, or piperazine.

A "cycloalkyl" group refers to an all-carbon monocyclic ring (i.e., rings which share an adjacent pair of carbon atoms) of 3 to 6 ring atoms wherein one of more of the rings does not have a completely conjugated pi-electron system e.g, cyclopropyl, cyclobutyl, cyclopentyl, cyclohexyl, cyclobutenyl, cyclopentenyl, cyclohexenyl, and the like. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is preferably one or more, more preferably one or two groups, individually selected from unsubstituted alkyl, alkyl, aryl, heteroaryl, unsubstituted heteroalicyclic, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —$NR^{13}R^{14}$, with $R^{13}$ and $R^{14}$ as defined above.

An "alkenyl" group refers to an alkyl group, as defined herein, consisting of at least two carbon atoms and at least one carbon-carbon double bond e.g., ethenyl, propenyl, butenyl or pentenyl and their structural isomeric forms such as 1- or 2-propenyl, 1-, 2-, or 3-butenyl and the like.

An "alkynyl" group refers to an alkyl group, as defined herein, consisting of at least two carbon atoms and at least one carbon-carbon triple bond e.g., acetylene, ethenyl, propynyl, butynyl, or pentenyl and their structural isomeric forms as described above.

An "aryl" group refers to an all-carbon monocyclic or fused-ring polycyclic (i.e., rings which share adjacent pairs of carbon atoms) groups of 6 to 12 ring atoms and having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two, or three substituents, independently selected from the group consisting of halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^{13}R^{14}$, with $R^{13}$ and $R^{14}$ as defined above. Preferably the substituent(s) is/are independently selected from chloro, fluoro, bromo, methyl, ethyl, propyl including all its isomeric forms, butyl including all its isomeric forms, hydroxy, methoxy, phenoxy, thio, methylthio, phenylthio, cyano, nitro, carboxy, methoxycarbonyl, or amino.

A "heteroaryl" group refers to a monocyclic or fused aromatic ring (i.e., rings which share an adjacent pair of atoms) of 5 to 9 ring atoms in which one, two, three or four ring atoms are selected from the group consisting of nitrogen, oxygen and sulfur and the rest being carbon. Examples, without limitation, of heteroaryl groups are pyrrole, furan, thiophene, imidazole, oxazole, thiazole, pyrazole, tetrazole, pyridine, pyrimidine, quinoline, isoquinoline, purine and carbazole. The heteroaryl group may be substituted or unsubstituted. When substituted, the substituted group(s) is preferably one or more, more preferably one or two substituents, independently selected from the group consisting of alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —$NR^{13}R^{14}$, with $R^{13}$ and $R^{14}$ as defined above. Preferably the substituent(s) is/are independently selected from chloro, fluoro, bromo, methyl, ethyl, propyl including all its isomeric forms, butyl including all its isomeric forms, hydroxy, methoxy, phenoxy, thio, methylthio, phenylthio, cyano, nitro, carboxy, methoxycarbonyl, or amino.

A "heteroalicyclic" group refers to a monocyclic or fused ring of 4 to 9 ring atoms containing one, two, or three heteroatoms in the ring which are selected from the group consisting of nitrogen, oxygen and —$S(O)_n$ where n is 0–2, the remaining ring atoms being carbon. The rings may also have one or more double bonds. However, the rings do not have a completely conjugated pi-electron system. Examples, without limitation, of heteroalicyclic groups are pyrrolidine, piperidine, piperazine, morpholine, imidazolidine, tetrahydropyridazine, tetrahydrofuran, thiomorpholine, tetrahydropyridine, and the like. The heteroalicyclic ring may be substituted or unsubstituted. When substituted, the substituted group(s) is preferably one or more, more preferably one, two, or three substituents, independently selected from the group consisting of alkyl, cycloalkyl, halo, trihalomethyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and —$NR^{13}R^{14}$, with $R^{13}$ and $R^{14}$ as defined above. Preferably the substituent(s) is/are independently selected from chloro, fluoro, bromo, methyl, ethyl, propyl including all its isomeric forms, butyl including all its isomeric forms, hydroxy, methoxy, phenoxy, thio, methylthio, phenylthio, cyano, nitro, carboxy, methoxycarbonyl, or amino.

A "hydroxy" group refers to an —OH group.

An "alkoxy" group refers to an —O-unsubstituted alkyl, —O-substituted alkyl and an —O-unsubstituted cycloalkyl group, as defined herein. Examples include and are not limited to methoxy, ethoxy, propoxy, butoxy, cyclopropyloxy, and the like, preferably methoxy.

An "aryloxy" group refers to both an —O-aryl and an —O-heteroaryl group, as defined herein. Examples include and are not limited to phenoxy, napthyloxy, pyridyloxy, furanyloxy, and the like.

A "mercapto" group refers to an —SH group.

An "alkylthio" group refers to both an S-alkyl and an —S-cycloalkyl group, as defined herein. Examples include and are not limited to methylthio, ethylthio, and the like.

A "arylthio" group refers to both an —S-aryl and an —S-heteroaryl group, as defined herein. Examples include and are not limited to phenylthio, napthylthio, pyridylthio, furanylthio, and the like.

A "sulfinyl" group refers to a —S(=O)—R" group wherein, in addition to being as defined below, R" may also be a hydroxy group, e.g., methylsulfinyl, phenylsulfinyl, and the like.

A "sulfonyl" group refers to a —$S(=O)_2R"$ group wherein, in addition to being as defined below, R" may also be a hydroxy group e.g., methylsulfonyl, ethylsulfonyl, phenylsulfonyl, and the like.

A "trihalomethyl" group refers to a —$CX_3$ group wherein X is a halo group as defined herein e.g., trifluoromethyl, trichloromethyl, tribromomethyl, dichlorofluoromethyl, and the like.

A "trihalomethanesulfonyl" group refers to a $X_3CS(=O)_2$— groups with X as defined above, e.g., trifluoromethylsulfonyl, trichloromethylsulfonyl, tribromomethylsulfonyl, and the like.

A "trihalomethanesulfonylamido" group refers to a —NH—$S(=O)_2R$ groups wherein R is trihalomethyl as defined above.

"Carbonyl" and "acyl" are used interchangeably herein to refer to a —C(=O)—R" group, where R" is selected from the group consisting of hydrogen, alkyl, cycloalkyl, aryl, heteroaryl (bonded through a ring carbon) and heteroalicyclic (bonded through a ring carbon), as defined herein. Representative examples include and are not limited to acetyl, propionyl, benzoyl, formyl, cyclopropylcarbonyl, pyridinylcarbonyl, pyrrolidin-1-ylcarbonyl, and the like.

An "aldehyde" group refers to a carbonyl group where R" is hydrogen.

A "thiocarbonyl" group refers to a —C(=S)—R" group, with R" as defined herein.

A "C-carboxy" group refers to a —C(=O)O—R" group, with R" as defined herein e.g., —COOH, methylcarbonyl, ethylcarbonyl, benzyloxycarbonyl, and the like.

An "O-carboxy" group refers to a —OC(=O)R" group, with R" as defined herein e.g., methylcarbonyloxy, phenylcarbonyloxy, benzylcarbonyloxy, and the like.

An "ester" group refers to a —C(=O)O—R" group with R" as defined herein except that R" cannot be hydrogen e.g., methoxycarbonyl, benzyloxycarbonyl, and the like.

An "acetyl" group refers to a —C(=O)CH$_3$ group.

A "carboxylic acid" group refers to a C-carboxy group in which R" is hydrogen.

A "halo" group refers to fluorine, chlorine, bromine or iodine.

A "cyano" group refers to a —C≡N group.

A "nitro" group refers to a —NO$_2$ group.

A "methylenedioxy" group refers to a —OCH$_2$O— group where the two oxygen atoms are bonded to adjacent carbon atoms.

An "ethylenedioxy" group refers to a —OCH$_2$CH$_2$O— where the two oxygen atoms are bonded to adjacent carbon atoms.

An "S-sulfonamido" group refers to a —S(=O)$_2$NR$^{13}$R$^{14}$ group, with R$^{13}$ and R$^{14}$ as defined herein. Representative examples include and are not limited to dimethylaminosulfonyl, aminosulfonyl, phenylmethylaminosulfonyl, phenylaminosulfonyl, and the like.

An "N-sulfonamido" group refers to a —NR$^{13}$S(=O)$_2$R$^{14}$ group, with R$^{13}$ and R$^{14}$ as defined herein e.g., methylsulfonylamino, ethylsulfonylamino, phenylsulfonylamino, benzylsulfonylamino, and the like.

An "O-carbamyl" group refers to a —OC(=O)NR$^{13}$R$^{14}$ group with R$^{13}$ and R$^{14}$ as defined herein.

An "N-carbamyl" group refers to a R$^{14}$OC(=O)NR$^{13}$— group, with R$^{13}$ and R$^{14}$ as defined herein.

An "O-thiocarbamyl" group refers to a —OC(=S)NR$^{13}$R$^{14}$ group with R$^{13}$ and R$^{14}$ as defined herein.

An "N-thiocarbamyl" group refers to a R$^{14}$OC(=S)NR$^{13}$— group, with R$^{13}$ and R$^{14}$ as defined herein.

An "amino" group refers to an —NR$^{13}$R$^{14}$ group, wherein R$^{13}$ and R$^{14}$ are independently hydrogen or unsubstituted alkyl e.g, —NH$_2$, dimethylamino, diethylamino, ethylamino, methylamino, phenylamino, and the like.

A "C-amido" group refers to a —C(=O)NR$^{13}$R$^{14}$ group with R$^{13}$ and R$^{14}$ as defined herein. Preferably R$^{13}$ is hydrogen or unsubstituted lower alkyl and R$^{14}$ is hydrogen, lower alkyl optionally substituted with heteroalicyclic, hydroxy, or amino. For example, —C(=O)NR$^{13}$R$^{14}$ may be aminocarbonyl, dimethylaminocarbonyl, diethylaminocarbonyl, diethylaminoethylaminocarbonyl, ethylaminoethylaminocarbonyl, 2-morpholinoethylaminocarbonyl, 3-morpholinopropylaminocarbonyl, 3-morpholino-2-hydroxypropylaminocarbonyl, and the like.

An "N-amido" group refers to a R$^{14}$C(=O)NR$^{13}$— group, with R$^{13}$ and R$^{14}$ as defined herein e.g., acetylamino, and the like.

A "ammonium" group refers to a —$^+$NR$^{15}$R$^{16}$R$^{17}$ group, wherein R$^{15}$ and R$^{16}$ are independently selected from the group consisting of alkyl, cycloalkyl, aryl, and heteroaryl, and R$^{17}$ is selected from the group consisting of hydrogen, alkyl, cycloalkyl, aryl, and heteroaryl.

A "amidino" group refers to a R$^{15}$R$^{16}$NC(=NR$^{17}$)— group, with R$^{15}$, R$^{16}$ and R$^{17}$ as defined above.

A "ureido" group refers to a —NR$^{17}$C(=O)NR$^{15}$R$^{16}$ group, with R$^{15}$, R$^{16}$ and R$^{17}$ as defined above.

A "guanidino" group refers to a —R$^{13}$NC(=NR$^{14}$)NR$^{15}$R$^{16}$ group, with R$^{13}$, R$^{14}$, R$^{15}$ and R$^{16}$ as defined above.

A "phosphonate" group refers to a —OP(=O)(OR)(OR'), with R and R' as defined herein.

A "tetrazolo" group refers to a group having the chemical structure:

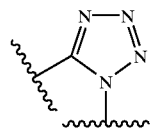

A "morpholino" group refers to a group having the chemical structure

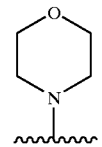

A "piperazinyl" group refers to a group having the chemical structure:

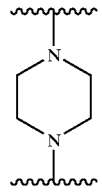

The terms "indolinone", "2-indolinone" and "indolin-2-one" are used interchangeably herein to refer to a molecule having the chemical structure:

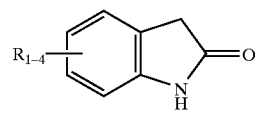

"Pyrrole" refers to a molecule having the chemical structure:

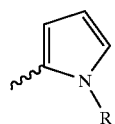

"Pyrrole-substituted 2-indolinone" and "3-pyrrol-1-yl-2-indolinone" are used interchangeably herein to refer to a chemical compound having the general structure shown below:

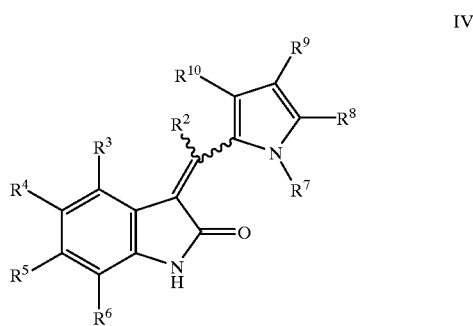

IV

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221–294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5(4):265–287 (1999); Pauletti et al. (1997) Improvement in peptide bioavailability: Peptidomimetics and Prodrug Strategies, Adv. Drug. Delivery Rev. 27:235–256; Mizen et al. (1998) "The Use of Esters as Prodrugs for Oral Delivery of β-Lactam antibiotics," Pharm. Biotech. 11,:345–365; Gaignault et al. (1996) "Designing Prodrugs and Bioprecursors I. Carrier Prodrugs," Pract. Med. Chem. 671–696; Asgharnejad, "Improving Oral Drug Transport", in Transport Processes in Pharmaceutical Systems, G. L. Amidon, P. I. Lee and E. M. Topp, Eds., Marcell Dekker, p. 185–218 (2000); Balant et al., "Prodrugs for the improvement of drug absorption via different routes of administration", Eur. J. Drug Metab. Pharmacokinet., 15(2): 143–53 (1990); Balimane and Sinko, "Involvement of multiple transporters in the oral absorption of nucleoside analogues", Adv. Drug Delivery Rev., 39(1–3): 183–209 (1999); Browne, "Fosphenytoin (Cerebyx)", Clin. Neuropharmacol. 20(1): 1–12 (1997); Bundgaard, "Bioreversible derivatization of drugs—principle and applicability to improve the therapeutic effects of drugs", Arch. Pharm. Chemi 86(1): 1–39 (1979); Bundgaard H. "Improved drug delivery by the prodrug approach", Controlled Drug Delivery 17: 179–96 (1987); Bundgaard H. "Prodrugs as a means to improve the delivery of peptide drugs", Adv. Drug Delivery Rev. 8(1): 1–38 (1992); Fleisher et al. "Improved oral drug delivery: solubility limitations overcome by the use of prodrugs", Adv. Drug Delivery Rev. 19(2): 115–130 (1996); Fleisher et al. "Design of prodrugs for improved gastrointestinal absorption by intestinal enzyme targeting", Methods Enzymol. 112 (Drug Enzyme Targeting, Pt. A): 360–81, (1985); Farquhar D, et al., "Biologically Reversible Phosphate-Protective Groups", J. Pharm. Sci., 72(3): 324–325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875–877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49–59 (1996); Gangwar et al., "Pro-drug, molecular structure and percutaneous delivery", Des. Biopharm. Prop. Prodrugs Analogs, [Symp.] Meeting Date 1976, 409–21. (1977); Nathwani and Wood, "Penicillins: a current review of their clinical pharmacology and therapeutic use", Drugs 45(6): 866–94 (1993); Sinhababu and Thakker, "Prodrugs of anticancer agents", Adv. Drug Delivery Rev. 19(2): 241–273 (1996); Stella et al., "Prodrugs. Do they have advantages in clinical practice?", Drugs 29(5): 455–73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1–3): 117–151 (1999); Taylor, "Improved passive oral drug delivery via prodrugs", Adv. Drug Delivery Rev., 19(2): 131–148 (1996); Valentino and Borchardt, "Prodrug strategies to enhance the intestinal absorption of peptides", Drug Discovery Today 2(4): 148–155 (1997); Wiebe and Knaus, "Concepts for the design of anti-HIV nucleoside prodrugs for treating cephalic HIV infection", Adv. Drug Delivery Rev.: 39(1–3):63–80 (1999); Waller et al., "Prodrugs", Br. J. Clin. Pharmac. 28: 497–507 (1989).

The compounds of this invention may possess one or more chiral centers, and can therefore be produced as individual stereoisomers or as mixtures of stereoisomers, depending on whether individual stereoisomers or mixtures of stereoisomers of the starting materials are used. Unless indicated otherwise, the description or naming of a compound or group of compounds is intended to include both the individual stereoisomers or mixtures (racemic or otherwise) of stereoisomers. Methods for the determination of stereochemistry and the separation of stereoisomers are well known to a person of ordinary skill in the art [see the discussion in Chapter 4 of March J: Advanced Organic Chemistry, 4th ed. John Wiley and Sons, New York, N.Y., 1992].

The chemical formulae referred to herein may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished in vitro, i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, ie., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, an isolated PK may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "PK related disorder," "PK driven disorder," and "abnormal PK activity" all refer to a condition characterized by inappropriate, i.e., under or, more commonly, over PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

The term "organism" refers to any living entity comprised of at least one cell. A living organism can be as simple as, for example, a single eukaryotic cell or as complex as a mammal, including a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or a pharmaceutically acceptable salts thereof, with other chemical components, such as physiologically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer, these terms simply mean that the life expectancy of an individual affected with a cancer will be increased or that one or more of the symptoms of the disease will be reduced.

By "monitoring" is meant observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. For example, the catalytic activity of a PK may be observed by determining the rate or amount of phosphorylation of a target molecule. The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue.

Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

Presently Preferred Embodiments

While the broadest definition of the invention is set out in the Summary of the Invention, certain compounds of this invention are presently preferred.

(A) A preferred group of compounds is represented by formula (I):

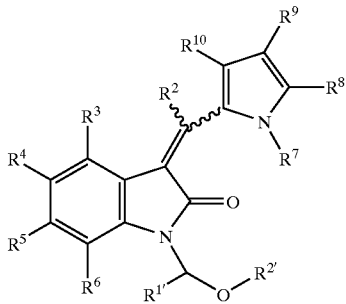

wherein:
$R^2$ is hydrogen;
$R^3$, $R^4$, $R^5$, and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino, and —$NR^{11}R^{12}$ where $R^{11}$ and $R^{12}$ are independently selected from the group consisting of hydrogen, alkyl, cycloalkyl, aryl, carbonyl, acetyl, sulfonyl, and trifluoromethanesulfonyl, or $R^{11}$ and $R^{12}$, together with the nitrogen atom to which they are attached, combine to form a five- or six-membered heteroalicyclic ring provided that at least two of $R^3$, $R^4$, $R^5$ and $R^6$ are hydrogen; or
$R^3$ and $R^4$, $R^4$ and $R^5$, or $R^5$ and $R^6$ combine to form a six-membered aryl ring, a methylenedioxy or an ethylenedioxy group;
$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethanesulfonyl;
$R^8$, $R^9$ and $R^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —$NR^{11}R^{12}$ wherein $R^{11}$ and $R^{12}$ are as defined above;
$R^{1'}$ is hydrogen or alkyl;
$R^{2'}$ is hydrogen, alkyl, aralkyl, acyl or —P(O)(OR)(OR') where R and R' are independently selected from the group consisting of hydrogen, alkyl, aralkyl or aryl; or a pharmaceutically acceptable salt thereof.

(a) In a preferred embodiment of formula I, $R^{2'}$ and $R^7$ are hydrogen.
Within this group a more preferred group of compounds is that wherein:
$R^3$ is hydrogen or lower unsubstituted alkyl, preferably hydrogen or methyl, more preferably hydrogen;
$R^4$ is selected from the group consisting of hydrogen, halogen, aryl and S-sulfonamido, preferably hydrogen, chloro, fluoro, bromo, phenyl, even more preferably hydrogen or fluoro, most preferably hydrogen;
$R^5$ is selected from the group consisting of hydrogen, lower alkyl, lower alkoxy, aryl, and heteroaryl, preferably hydrogen, methyl, ethyl, methoxy, phenyl, pyridyl, more preferably hydrogen; and
$R^{1'}$ and $R^6$ hydrogen.
Within the above preferred and more preferred groups an even more preferred group of compounds is that wherein:
$R^8$ and $R^{10}$ are unsubstituted lower alkyl, preferably methyl; and $R^9$ is hydrogen, C-amido, or -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl), preferably hydrogen, 2-(dimethylaminoethyl)aminocarbonyl, 2-(diethylaminoethyl)aminocarbonyl, 2-(pyrrolidin-1-ylethyl)aminocarbonyl, 2-(morpholin-4-ylethyl)aminocarbonyl, or 3-carboxypropyl, more preferably hydrogen.
Particularly preferred compounds within this group are:
(3Z)-3-[(3,5-dimethyl-1H-pyrrol-2-yl)-methylidene]-1-(hydroxymethyl)-1,3-dihydro-2H-indol-2-one (1) and 3-[5-{(Z)-[1-(hydroxymethyl)-1,2-dihydro-3H-indol-3-ylidine]methyl}-2,4-dimethyl-1H-pyrrole-3-propanoic acid (5).

(b) Another preferred group of compounds of formula I is that wherein:
$R^{2'}$ is —P(O)(OR)(OR') and $R^7$ is hydrogen.
Within this group a more preferred group of compounds is that wherein:
$R^3$ is hydrogen or lower unsubstituted alkyl, preferably hydrogen or methyl, more preferably hydrogen;
$R^4$ is selected from the group consisting of hydrogen, halogen, aryl and S-sulfonamido, preferably hydrogen, chloro, fluoro, bromo, phenyl, even more preferably hydrogen or fluoro, most preferably hydrogen;
$R^5$ is selected from the group consisting of hydrogen, lower alkyl, lower alkoxy, aryl, and heteroaryl, preferably hydrogen, methyl, ethyl, methoxy, phenyl, pyridyl, more preferably hydrogen; and $R^{1'}$ and $R^6$ are hydrogen.

Within the above preferred and more preferred groups an even more preferred group of compounds is that wherein:

$R^8$ and $R^{10}$ are unsubstituted lower alkyl, preferably methyl; and $R^9$ is hydrogen, C-amido, or -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl), preferably hydrogen, 2-(dimethylaminoethyl)aminocarbonyl, 2-(diethylaminoethyl)aminocarbonyl, 2-(pyrrolidin-1-ylethyl)aminocarbonyl, 2-(morpholin-4-ylethyl) aminocarbonyl, or 3-carboxypropyl, more preferably hydrogen.

Within this group, particularly preferred compounds are {(3Z)-3-[(3,5-dimethyl-1H-pyrrol-2-yl)methylidene]-2-oxo-2,3-dihydro-1H-indol-1-yl}methyl dihydrogen phosphate (7) and {(3Z)-3-[(3,5-dimethyl-4-(3-carboxypropyl)-1H-pyrrol-2-yl)methylidene]-2-oxo-2,3-dihydro-1H-indol-1-yl}methyl dihydrogen phosphate.

(c) Yet another preferred group of compounds of formula I is that wherein $R^{2'}$ is acyl and $R^7$ is hydrogen.

Within this group a more preferred group of compounds is that wherein:

$R^3$ is hydrogen or lower unsubstituted alkyl, preferably hydrogen or methyl, more preferably hydrogen;

$R^4$ is selected from the group consisting of hydrogen, halogen, aryl and S-sulfonamido, preferably hydrogen, chloro, fluoro, bromo, phenyl, even more preferably hydrogen or fluoro, most preferably hydrogen;

$R^5$ is selected from the group consisting of hydrogen, lower alkyl, lower alkoxy, aryl, and heteroaryl, preferably hydrogen, methyl, ethyl, methoxy, phenyl, pyridyl, more preferably hydrogen; and $R^{1'}$ and $R^6$ are hydrogen.

Within the above preferred and more preferred groups an even more preferred group of compounds is that wherein:

$R^8$ and $R^{10}$ are unsubstituted lower alkyl, preferably methyl; and $R^9$ is hydrogen, C-amido, or -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl), preferably hydrogen, 2-(dimethylaminoethyl)aminocarbonyl, 2-(diethylaminoethyl)aminocarbonyl, 2-(pyrrolidin-1-ylethyl)aminocarbonyl, 2-(morpholin-4-ylethyl) aminocarbonyl, or 3-carboxypropyl, more preferably hydrogen.

Within this group, particularly preferred compounds are 4-({(3Z)-3-[(3,5-dimethyl-1H-pyrrol-2-yl)-methylidene]-2-oxo-2,3-dihydro-1H-indol-1-yl}methoxy)-4-oxobutanoic acid (3) and 4-({(3Z)-3-[(3,5-dimethyl-4-(3-carboxypropyl)-1H-pyrrol-2-yl)-methylidene]-2-oxo-2,3-dihydro-1H-indol-1-yl}methoxy)-4-oxobutanoic acid.

(B) Another preferred group of compounds is represented by formula (II):

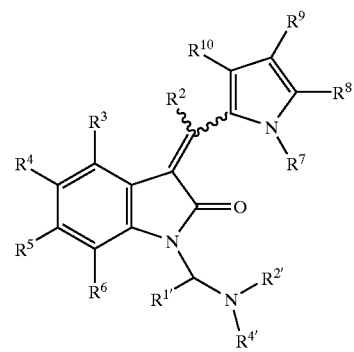

wherein:

$R^2$ is hydrogen;

$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$ where R$^{11}$ and R$^{12}$ are independently selected from the group consisting of hydrogen, alkyl, cycloalkyl, aryl, carbonyl, acetyl, sulfonyl, and trifluoromethanesulfonyl, or R$^{11}$ and R$^{12}$, together with the nitrogen atom to which they are attached, combine to form a five- or six-membered heteroalicyclic ring provided that at least two of R$^3$, R$^4$, R$^5$ and R$^6$ are hydrogen; or $R^3$ and $R^4$, $R^4$ and $R^5$, or $R^5$ and $R^6$ combine to form a six-membered aryl ring, a methylenedioxy or an ethylenedioxy group;

$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethanesulfonyl;

$R^8$, $R^9$ and $R^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —NR$^{11}$R$^{12}$ wherein R$^{11}$ and R$^{12}$ are as defined above;

R$^{1'}$ is hydrogen or alkyl; and $R^{3'}$ and $R^{4'}$ are independently alkyl or together with the nitrogen atom to which they are attached combine to form a heteroalicyclic ring or a heteroaryl ring; or a pharmaceutically acceptable salt thereof; with the proviso that $R^{3'}$ and $R^{4'}$ are not morpholin-1-yl or piperidin-1-yl.

Presently preferred compounds of formula II are:

$R^3$ is hydrogen or lower unsubstituted alkyl, preferably hydrogen or methyl, more preferably hydrogen;

R⁴ is selected from the group consisting of hydrogen, halogen, aryl and S-sulfonamido, preferably hydrogen, chloro, fluoro, bromo, phenyl, even more preferably hydrogen or fluoro, most preferably hydrogen;

R⁵ is selected from the group consisting of hydrogen, lower alkyl, lower alkoxy, aryl, and heteroaryl, preferably hydrogen, methyl, ethyl, methoxy, phenyl, pyridyl, more preferably hydrogen; and R⁶ is hydrogen;

R⁷ is hydrogen;

R' is hydrogen or methyl, especially hydrogen;

R⁸ and R¹⁰ are independently unsubstituted lower alkyl, especially methyl;

R⁹ is hydrogen, lower alkyl substituted with C-carboxy, —C(=O)NHR¹² wherein R¹² is lower alkyl substituted with amino or heteroalicyclic and optionally substituted with hydroxy; R⁹ is preferably hydrogen, 3-carboxypropyl, (2-diethylaminoethyl)-aminocarbonyl, (2-ethylaminoethyl)aminocarbonyl, 2-(pyrrolidin-1-ylethyl)-aminocarbonyl, 3-(morpholin-4-yl)propyl-aminocarbonyl, 3-(morpholin-4-yl)-2-hydroxypropylaminocarbonyl; R⁹ is most preferably hydrogen, 3-carboxypropyl, (2-diethylaminoethyl) aminocarbonyl, or (2-ethylaminoethyl)-aminocarbonyl; and R³' and R⁴' are lower alkyl optionally substituted hydroxy, especially methyl, ethyl, 2-hydroxyethyl; or R³' and R⁴', together with the nitrogen atom to which they are attached, form pyrrolidin-1-yl, 2-(S)-hydroxymethylpyrrolidin-1-yl, 2-(S)-carboxypyrrolidin-1-yl, piperazin-1-yl, or 4-methylpiperazin-1-yl, especially pyrrolidin-1-yl; or R³' and R⁴', together with the nitrogen atom to which they are attached form a heteroaryl ring, preferably, pyrro-1-yl, pyridin-1-yl, oxazol-3-yl, isoxazol-2-yl, pyrazin-1-yl, pyradizin-1-yl, quinolin-1-yl, imidazol-1-yl, more preferably pyridin-1-yl.

A number of different preferences have been given above, and following any one of these preferences results in a compound of this invention that is more presently preferred than a compound in which that particular preference is not followed. However, these preferences are generally independent [although some (alternative) preferences are mutually exclusive], and additive; and following more than one of these preferences may result in a more presently preferred compound than one in which fewer of the preferences are followed.

Presently preferred classes of compounds of formula II include those where:

(a) R¹', R³, R⁴, R⁵, R⁶, R⁷, and R⁹ are hydrogen; R⁸ and R¹⁰ are unsubstituted lower alkyl, especially methyl; and R³' and R⁴', together with the nitrogen atom to which they are attached, form pyrrolidin-1-yl, 2-(S)-hydroxymethylpyrrolidin-1-yl, 2-(S)-carboxypyrrolidin-1-yl, piperazin-1-yl, or 4-methylpiperazin-1-yl, especially pyrrolidin-1-yl.

(b) R¹', R³, R⁴, R⁵, R⁶, and R⁷ are hydrogen; R⁸ and R¹⁰ are unsubstituted lower alkyl, especially methyl; R⁹ is lower alkyl substituted with C-carboxy, especially 3-carboxypropyl; and R³' and R⁴', together with the nitrogen atom to which they are attached, form pyrrolidin-1-yl, 2-(S)-hydroxymethylpyrrolidin-1-yl, 2-(S)-carboxypyrrolidin-1-yl, piperazin-1-yl, or 4-methylpiperazin-1-yl, especially pyrrolidin-1-yl.

(c) R¹', R³, R⁵, R⁶, and R⁷ are hydrogen; R⁴ is halo, especially fluoro, R⁸ and R¹⁰ are unsubstituted lower alkyl, especially methyl; R⁹ is —C(=O)NHR¹³ wherein R¹³ is lower alkyl substituted with amino or heteroalicyclic and optionally substituted with hydroxy, especially (2-diethylaminoethyl)-aminocarbonyl, (2-ethylaminoethyl)-aminocarbonyl, 2-(pyrrolidin-1-ylethyl)aminocarbonyl, 3-(morpholin-4-yl)propyl-aminocarbonyl, 3-(morpholin-4-yl)-2-hydroxypropylaminocarbonyl, particularly (2-diethylaminoethyl)aminocarbonyl, or (2-ethylaminoethyl)-aminocarbonyl; and R³' and R⁴', together with the nitrogen atom to which they are attached, form pyrrolidin-1-yl, 2-(S)-hydroxymethylpyrrolidin-1-yl, 2-(S)-carboxypyrrolidin-1-yl, piperazin-1-yl, or 4-methylpiperazin-1-yl, especially pyrrolidin-1-yl.

(d) R¹', R³, R⁴, R⁵, R⁶, R⁷, and R⁹ are hydrogen; R⁸ and R¹⁰ are unsubstituted lower alkyl, especially methyl; and R³' and R⁴', together with the nitrogen atom to which they are attached, form a heteroaryl ring, preferably, pyrrol-1-yl, pyridin-1-yl, oxazol-3-yl, isoxazol-2-yl, pyrazin-1-yl, pyridazin-1-yl, quinolin-1-yl, imidazol-1-yl, more preferably pyridin-1-yl.

Presently preferred compounds of formula II include:
(3Z)-3-[(3,5-dimethyl-1H-pyrrol-2-yl)-methylidene]-1-(1-pyrrolidinylmethyl)-1,3-dihydro-2H-indol-2-one (14); (3Z)-3-[(3,5-dimethyl-1H-pyrrol-2-yl)-methylidene]-1-(4-methylpiperazin-1-ylmethyl)-1,3-dihydro-2H-indol-2-one (13); (3Z)-3-[(3,5-dimethyl-1H-pyrrol-2-yl)-methylidene]-1-[2(S)-hydroxymethyl-1-pyrrolidinylmethyl)-1,3-dihydro-2H-indol-2-one; (3Z)-3-[(3,5-dimethyl-1H-pyrrol-2-yl)-methylidene]-1-[2(S)-carboxy-1-pyrrolidinylmethyl)-1,3-dihydro-2H-indol-2-one; (3Z)-3-{[3,5-dimethyl-4-(2-diethylaminoethylaminocarbonyl)-1H-pyrrol-2-yl]-methylidene}-1-(1-pyrrolidinylmethyl)-1,3-dihydro-2H-indol-2-one; (3Z)-3-{[3,5-dimethyl-4-(2-ethylaminoethylaminocarbonyl)-1H-pyrrol-2-yl]-methylidene}-1-(1-pyrrolidinylmethyl)-1,3-dihydro-2H-indol-2-one; and (3Z)-3-{[3,5-dimethyl-4-(3-morpholin-4-yl-2-hydroxypropylaminocarbonyl)-1H-pyrrol-2-yl]-methylidene}-1-(1-pyrrolidinylmethyl)-1,3-dihydro-2H-indol-2-one; and 1-({(3Z)-3-[(3,5-dimethyl-1H-pyrrol-2-yl)-methylidene]-2-oxo-1,3-dihydro-1H-indol-1-yl}methyl)pyridinium chloride (12).

(C) Another preferred group of compounds is represented by formula III:

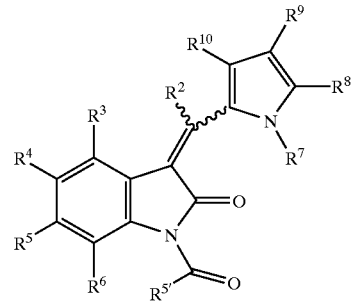

wherein:
R² is hydrogen;
R³, R⁴, R⁵ and R⁶ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$ where R$^{11}$ and R$^{12}$ are independently selected from the group consisting of hydrogen, alkyl, cycloalkyl, aryl, carbonyl, acetyl, sulfonyl, and trifluoromethanesulfonyl, or R$^{11}$ and R$^{12}$, together with the nitrogen atom to which they are attached, combine to form a five- or six-membered heteroalicyclic ring provided that at least two of R$^3$, R$^4$, R$^5$ and R$^6$ are hydrogen; or R$^3$ and R$^4$, R$^4$ and R$^5$, or R$^5$ and R$^6$ combine to form a six-membered aryl ring, a methylenedioxy or an ethylenedioxy group;

R$^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethanesulfonyl;

R$^8$, R$^9$ and R$^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —NR$^{11}$R$^{12}$ wherein R$^{11}$ and R$^{12}$ are as defined above; and R$^{5'}$ is alkyl; or a pharmaceutically acceptable salt thereof.

Within this group a more preferred group of compounds is that wherein:

R$^3$ is hydrogen or lower unsubstituted alkyl, preferably hydrogen or methyl, more preferably hydrogen;

R$^4$ is selected from the group consisting of hydrogen, halogen, aryl and S-sulfonamido, preferably hydrogen, chloro, fluoro, bromo, phenyl, even more preferably hydrogen or fluoro, most preferably hydrogen;

R$^5$ is selected from the group consisting of hydrogen, lower alkyl, lower alkoxy, aryl, and heteroaryl, preferably hydrogen, methyl, ethyl, methoxy, phenyl, pyridyl, more preferably hydrogen; and R$^6$ and R$^7$ are hydrogen.

Within the above preferred and more preferred groups an even more preferred group of compounds is that wherein:

R$^8$ and R$^{10}$ are unsubstituted lower alkyl, preferably methyl; and R$^9$ is hydrogen, C-amido, or -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl), preferably hydrogen, 2-(dimethylaminoethyl)aminocarbonyl, 2-(diethylaminoethyl)aminocarbonyl, 2-(pyrrolidin-1-ylethyl)aminocarbonyl, 2-(morpholin-4-ylethyl)aminocarbonyl, or 3-carboxypropyl, more preferably hydrogen.

Within the above preferred group, a more preferred group of compounds III is that wherein R$^{5'}$ is alkyl substituted with NR$^{11}$R$^{12}$ where R$^{11}$ and R$^{12}$ are as defined above, or ammonium.

Particularly preferred compounds of formula III are 2-{(3Z)-3-[(3,5-dimethyl-1H-pyrrol-2-yl)-methylidene]-2-oxo-2,3-dihydro-1H-indol-1-yl}-N,N,N-trimethyl-2-oxo-1-ethanaminium chloride (18) and 2-{(3Z)-3-[(3,5-dimethyl-4-(3-carboxypropyl)-1H-pyrrol-2-yl)-methylidene]-2-oxo-2,3-dihydro-1H-indol-1-yl}-N,N,N-trimethyl-2-oxo-1-ethanaminium chloride.

(D) Yet another preferred group of compounds is represented by formula IV:

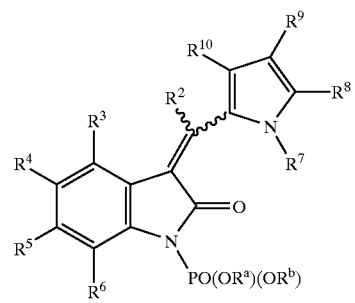

wherein:

R$^2$ is hydrogen;

R$^3$, R$^4$, R$^5$ and R$^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$ where R$^{11}$ and R$^{12}$ are independently selected from the group consisting of hydrogen, alkyl, cycloalkyl, aryl, carbonyl, acetyl, sulfonyl, and trifluoromethanesulfonyl or R$^{11}$ and R$^{12}$ together with the nitrogen atom to which they are attached combine to form a five- or six-membered heteroalicyclic ring provided that at least two of R$^3$, R$^4$, R$^5$ and R$^6$ are hydrogen; or R$^3$ and R$^4$, R$^4$ and R$^5$, or R$^5$ and R$^6$ combine to form a six-membered aryl ring, a methylenedioxy or an ethylenedioxy group;

R$^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethanesulfonyl;

R$^8$, R$^9$ and R$^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —NR$^{11}$R$^{12}$ wherein R$^{11}$ and R$^{12}$ are as defined above; and R$^a$ and R$^b$ are independently selected from hydrogen or alkyl; or a pharmaceutically acceptable salt thereof.

Within this group a more preferred group of compounds is that wherein:

$R^3$ is hydrogen or lower unsubstituted alkyl, preferably hydrogen or methyl, more preferably hydrogen;

$R^4$ is selected from the group consisting of hydrogen, halogen, aryl and S-sulfonamido, preferably hydrogen, chloro, fluoro, bromo, phenyl, even more preferably hydrogen or fluoro, most preferably hydrogen;

$R^5$ is selected from the group consisting of hydrogen, lower alkyl, lower alkoxy, aryl, and heteroaryl, preferably hydrogen, methyl, ethyl, methoxy, phenyl, pyridyl, more preferably hydrogen; and $R^6$ and $R^7$ are hydrogen.

Within the above preferred and more preferred groups an even more preferred group of compounds is that wherein:

$R^8$ and $R^{10}$ are unsubstituted lower alkyl, preferably methyl; and $R^9$ is hydrogen, C-amido, or -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl), preferably hydrogen, 2-(dimethylaminoethyl)aminocarbonyl, 2-(diethylaminoethyl)aminocarbonyl, 2-(pyrrolidin-1-ylethyl)aminocarbonyl, 2-(morpholin-4-ylethyl)aminocarbonyl, or 3-carboxypropyl, more preferably hydrogen.

Within the above preferred group, a more preferred group of compounds IV is that wherein $R^a$ and $R^b$ are independently hydrogen or unsubstituted lower alkyl, preferably hydrogen or methyl, most preferably hydrogen.

Particularly preferred compounds of formula IV are (3Z)-3-[(3,5-dimethyl-1H-pyrrol-2-yl)-methylidene]-1-(dimethylphosphonyl)-1,3-dihydro-2H-indol-2-one, (3Z)-3-[(3,5-dimethyl-1H-pyrrol-2-yl)-methylidene]-1-(phosphonyl)-1,3-dihydro-2H-indol-2-one, (3Z)-3-[(3,5-dimethyl-4-(3-carboxypropyl)-1H-pyrrol-2-yl)-methylidene]-1-(dimethylphosphonyl)-1,3-dihydro-2H-indol-2-one, and (3Z)-3-[(3,5-dimethyl-4-(3-carboxypropyl)-1H-pyrrol-2-yl)-methylidene]-1-(phosphonyl)-1,3-dihydro-2H-indol-2-one.

Other preferred group of compounds of this invention are those wherein:

$R^2$ is hydrogen.

$R^7$ is hydrogen.

$R^3$, $R^4$, $R^5$ and $R^6$ are selected from the group consisting of hydrogen, unsubstituted lower alkyl, lower alkyl substituted with a group selected from the group consisting of hydroxy, halo, C-carboxy substituted with a group selected from the group consisting of hydrogen and unsubstituted lower alkyl, amino, or —NR$^{11}$R$^{12}$; unsubstituted lower alkyl alkoxy, lower alkoxy substituted with one or more halo groups, lower alkoxy substituted with a group consisting of unsubstituted aryl or aryl substituted with one or more groups independently selected from the group consisting of unsubstituted lower alkyl, hydroxy, unsubstituted lower alkyl alkoxy, halo, amino, unsubstituted lower alkyl S-sulfonamido or —NR$^{11}$R$^{12}$, unsubstituted aryl or aryl substituted with one or more groups independently selected from the group consisting of unsubstituted lower alkyl, unsubstituted lower alkyl alkoxy, lower alkoxy substituted with one or more halo groups, lower alkoxy substituted with a group selected from the group consisting of unsubstituted aryl or aryl substituted with one or more groups independently selected from the group consisting of unsubstituted lower alkyl, hydroxy, unsubstituted lower alkyl alkoxy, halo, amino, unsub-
stituted lower alkyl S-sulfonamido or —NR$^{11}$R$^{12}$, hydroxy, amino, unsubstituted lower alkyl sulfonamido, C-carboxy substituted with a groups selected from the group consisting of hydrogen or unsubstituted lower alkyl, morpholino, —NR$^{11}$R$^{12}$, trihalomethyl, aryl, aryl substituted with one or more groups independently selected from the group consisting of hydroxy, halo, trihalomethyl, amino, —NR$^{11}$R$^{12}$, sulfonamido, C-carboxy substituted with a group selected from the group consisting of hydrogen or unsubstituted lower alkyl, unsubstituted lower alkyl or lower alkyl substituted with a group selected from the group consisting of hydroxy, halo, C-carboxy substituted with a group selected from the group consisting of hydrogen or unsubstituted lower alkyl, amino or —NR$^{11}$R$^{12}$, unsubstituted heteroalicyclic, heteroalicyclic substituted with one or more groups independently selected from the group consisting of halo, hydroxy, unsubstituted lower alkyl, unsubstituted lower alkyl carbonyl, hydroxy, unsubstituted lower alkyl alkoxy or alkoxy substituted with one or more halo groups, unsubstituted aryloxy, aryloxy substituted with one or more groups independently selected from the group consisting of unsubstituted lower alkyl, trihalomethyl, halo, hydroxy, amino or —NR$^{11}$R$^{12}$, mercapto, unsubstituted lower alkyl alkylthio, unsubstituted arylthio, arylthio substituted with one or more groups selected from the group consisting of halo, hydroxy, amino or —NR$^{11}$R$^{12}$, C-carboxy substituted with a group selected from the group consisting of hydrogen and unsubstituted lower alkyl, unsubstituted lower alkyl O-carboxy, unsubstituted lower alkyl S-sulfonamido, nitro, unsubstituted lower alkyl C-amido, unsubstituted lower alkyl N-amido, amino and —NR$^{11}$R$^{12}$.

More preferably, $R^3$, $R^4$, $R^5$ and $R^6$ are independently selected from the group consisting of hydrogen, halo, unsubstituted lower alkyl, lower alkyl substituted with one or more groups selected from the group consisting of hydroxy, halo, C-carboxy substituted with a group selected from the group consisting of hydrogen or unsubstituted lower alkyl, amino or —NR$^{11}$R$^{12}$, unsubstituted lower alkyl alkoxy, lower alkyl alkoxy substituted with one or more halo groups, unsubstituted aryloxy, aryloxy substituted with one or more groups independently selected from the group consisting of unsubstituted lower alkyl, lower alkyl substituted with one or more halo groups, hydroxy, unsubstituted lower alkyl alkoxy, halo, amino or —NR$^{11}$R$^{12}$, S-sulfonamido wherein R$^{11}$ and R$^{12}$ are independently selected from the group consisting of hydrogen and unsubstituted lower alkyl, unsubstituted aryl, aryl substituted with one or more groups independently selected from the group consisting of halo, unsubstituted lower alkyl, lower alkyl substituted with one or more halo groups, unsubstituted lower alkyl alkoxy, amino or —NR$^{11}$R$^{12}$, unsubstituted heteroaryl, heteroaryl substituted with one or more groups independently selected from the group consisting of unsubstituted lower alkyl, lower alkyl substituted with one or more halo groups, unsubstituted lower alkyl alkoxy, hydroxy, halo, amino or —NR$^{11}$R$^{12}$, unsubstituted heteroalicyclic, heteroalicyclic substituted with one or more groups independently selected from the group consisting of halo, hydroxy, unsubstituted lower alkyl, lower alkyl substituted with one or more halo groups, unsubstituted lower alkyl alkoxy, amino or —NR$^{11}$R$^{12}$, unsubstituted lower alkyl O-carboxy, C-amido wherein R$^{11}$ and R$^{12}$ are independently selected from the group consisting of hydrogen, unsubstituted lower alkyl and unsubstituted aryl, and, N-amido wherein R$^{11}$ and R$^{12}$ are independently selected from the group consisting of hydrogen, unsubstituted lower alkyl and unsubstituted aryl. Even more preferably, $R^3$ $R^4$, $R^5$, and $R^6$ are independently selected from the group consisting of hydrogen, halo, unsubstituted lower alkyl, lower alkyl substituted with one or more hydroxy groups, unsubstituted lower alkoxy, unsubstituted aryl, aryl substituted with one or more unsubstituted lower alkoxy groups, and —S(O)$_2$NR$^{11}$R$^{12}$, $R^5$ is hydrogen, $R^6$ is —NR$^{11}$R$^{12}$, and $R^{11}$ and $R^{12}$ are independently selected from the group consisting of hydrogen, unsubstituted lower alkyl and, $R^{11}$ and $R^{12}$, together with the nitrogen to which they are attached, combine to form a five-member or a six-member unsubstituted heteroalicyclic ring. Particularly preferably, $R^3$, $R^4$, $R^5$ and $R^6$ are all hydrogen or $R^3$, $R^5$ and $R^6$ are hydrogen and $R^4$ is halo, preferably chloro, bromo or fluoro, more preferably fluoro.

$R^8$, $R^9$ and $R^{10}$ may be -(alk$_1$)Z while the other two are independently selected from the group consisting of hydrogen, hydroxy, unsubstituted lower alkyl, unsubstituted lower alkenyl, unsubstituted lower alkynyl, unsubstituted lower alkyl alkoxy, lower alkoxy substituted with one or more halo groups, unsubstituted aryl alkoxy, amino, —NR$^{11}$R$^{12}$, halo, C-carboxy substituted with a groups selected from the group consisting of hydrogen or unsubstituted lower alkyl, unsubstituted lower alkyl O-carboxy, unsubstituted lower alkyl C-amido, unsubstituted lower alkyl N-amido, acetyl, unsubstituted lower alkyl S-sulfonamido, unsubstituted aryl or aryl substituted with a group selected from the group consisting of halo, hydroxy, unsubstituted lower alkyl alkoxy, alkoxy substituted with one or more halo groups, C-carboxy substituted with a groups selected from the group consisting of hydrogen or unsubstituted lower alkyl, unsubstituted lower alkyl O-carboxy, amino, unsubstituted lower alkyl S-sulfonamido and —NR$^{11}$R$^{12}$, preferably alk$_1$ is an unsubstituted lower alkyl group (more preferably 2 to 4 carbon atoms) and Z is selected from the group consisting of hydroxy, amino, —NR$^{11}$R$^{12}$, quaternary ammonium, C-carboxy substituted with a group selected from the group consisting of hydrogen or unsubstituted lower alkyl, C-amido substituted with groups selected from the group consisting of hydrogen and unsubstituted lower alkyl, morpholino, piperadinyl, tetrazolo and phosphonyl. Preferably, $R^8$ and $R^{10}$ are selected from the groups consisting of hydrogen and unsubstituted lower alkyl, $R^9$ is selected from the group consisting of hydrogen and alk$_1$Z.

It is likewise a presently preferred feature of this invention that $R^{11}$ and $R^{12}$ are independently selected from the group comprising hydrogen, unsubstituted lower alkyl, hydroxy, unsubstituted lower alkyl alkoxy, unsubstituted lower alkyl carbonyl, unsubstituted lower alkyl O-carboxy and acetyl.

It is also a presently preferred embodiment of this invention that Z is selected from the group consisting of —C(=O) NR$^{11}$R$^{12}$ wherein $R^{11}$ and $R^{12}$ are independently selected from the group consisting of hydrogen, unsubstituted lower alkyl, lower alkyl substituted with a group selected from the group consisting of amino and —NR$^{11}$R$^{12}$, unsubstituted aryl, aryl substituted with one or more groups selected from the group consisting of halo, hydroxy, unsubstituted lower alkyl alkoxy and trihalomethyl, unsubstituted heteroaryl, unsubstituted heteroalicyclic, and $R^{11}$ and $R^{12}$, together with the nitrogen to which they are attached, combine to form a five-member or a six-member unsubstituted heteroalicyclic, and, —NR$^{11}$R$^{12}$, wherein, $R^{11}$ and $R^{12}$ are independently selected from the group consisting of unsubstituted lower alkyl and, combined, a five-member or a six-member unsubstituted heteroalicyclic ring.

General Synthetic Scheme

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989); Organic Reactions, Volumes 1–40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data. Unless specified to the contrary, the reactions described herein take place at atmospheric pressure over a temperature range from about −78. degree °C. to about 150° C., more preferably from about 0° C. to about 125° C. and most preferably at about room (or ambient) temperature, e.g., about 20° C.

Compounds of Formula I can be prepared as illustrated and described below:

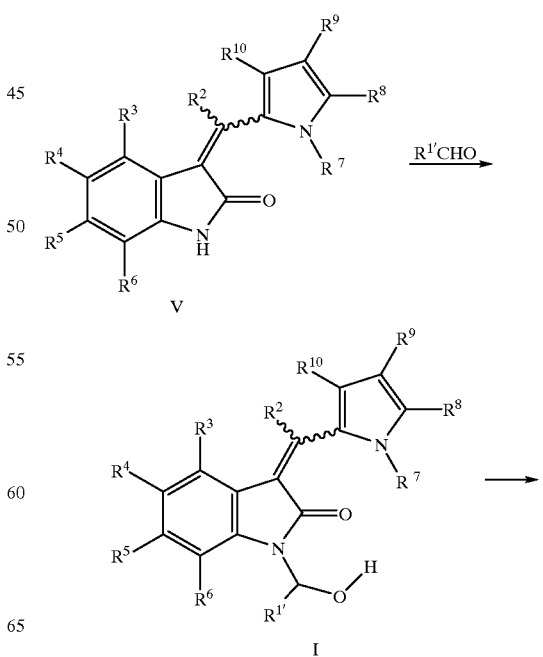

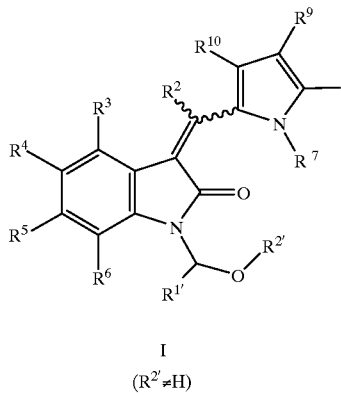

I
($R^{2'} \neq H$)

Compounds of Formula I where $R^{2'}$ is hydrogen can be readily prepared from compounds of Formula V by condensing V with a suitable aldehyde of formula $R^{1'}CHO$. The reaction may be carried out in the presence of an organic base, preferably a tertiary nitrogen base such as trimethylamine, triethylamine, pyridine, diisopropylethylamine, 1,8-diazabicyclo-[5.4.1]-undec-7-ene, and the like. The solvent in which the reaction is carried out may be an aprotic solvent. Examples, without limitation, include pentane, hexane, benzene, toluene, methylene chloride, carbon tetrachloride, chloroform, tetrahydrofuran (THF), dimethylsulfoxide (DMSo), dimethylformamide (DMF), pyridine, and the like. In a presently preferred embodiment of this invention, the solvent is a polar aprotic protic solvent, preferably acetonitrile, dimethylformamide, tetrahydrofuran or pyridine. The reaction may be carried out at room temperature. Aldehydes of formula $R^{1'}CHO$ are commerically available or they can be prepared by methods well known in the art. Some such examples, include but are not limited to, formaldehyde, acetaldehyde, proponaldehyde, an butyraldehyde are commercially available.

A compound of Formula I where $R^{2'}$ is hydrogen can be converted to other compounds of Formula I where $R^{2'}$ is alkyl, aralkyl, aryl, acyl or —P(O)(OR)(OR') by methods well known in the art. Some such methods are described below.

A compound of Formula I where $R^{2'}$ is alkyl or aralkyl can be prepared by reacting I where $R^{2'}$ is hydrogen with an alkylating agent of the formula $R^{2'}X$ where $R^{2'}$ is alkyl or aralkyl and X is a suitable leaving group such as halo, tosylate or mesylate, triflate, and the like, in the presence of a base such as triethylamine, pyridine, and the like. Alkylating agents such as methyl bromide, methyl iodide, benzyl bromide, benzyl iodide, 2-phenylethyl chloride, ethyl bromide are commercially available.

A compound of Formula I where $R^{2'}$ is acyl can be prepared by reacting by reacting I where $R^{2'}$ is hydrogen with an acylating agent such as acid anhydride e.g., acetic anhydride, succinic anhydride, and the like, acid halides such as acetyl chloride, propionyl chloride, butryl chloride an the like and carboxylic acid active esters such as p-nitrophenyl ester, pentafluorophenyl ester, and the like. The reaction is carried out in an organic base such as pyridine, DMAP, and the like. The reaction is carried out at ambient temperature. Alternatively, compounds of Formula I, where $R^{2'}$ is acyl may be prepared by reacting the parent 3-pyrrolidinyl-2-indolinone (V) with a suitable aldehyde such as formaldehyde, acetaldehyde and the like, in the presence of a suitable acylating agent $R^{2'}X$ discussed above, without isolating the intermediate N-hydroxyalkyl derivative of V.

A compound of Formula I where $R^{2'}$ is —P(O)(OR)(OR') where R and R' are not hydrogen can be prepared by reacting by reacting I where $R^{2'}$ is hydrogen with a phosphorylating agent in an organic base such as triethylamine, pyridine, and the like. Phosphorylating agent such as dibenzyl phosphorochloridate and benzyl methyl phosphorochloridate are commercially available. A compound of Formula I where R and R' are hydrogen can be prepared from a corresponding compound of Formula I where R and R' are benzyl by removal of the benzyl groups under hydrogenation reaction conditions. The reaction may be carried out in the presence of a base. The base may be an organic or an inorganic base. If an organic base is used, preferably it is a tertiary nitrogen base, or an alkali metal alkoxide, e.g., sodium methoxide. Examples of tertiary nitrogen bases include, but are not limited to, trimethylamine, triethylamine, pyridine, and 1,8-diazabicyclo[5.4.1]undec-7-ene. Examples of inorganic bases are, without limitation, alkali metal hydrides such as sodium hydride and alkali metal hydroxides such as sodium methoxide.

The solvent in which the reaction is carried out may be an aprotic solvent such as dimethylformamide, tetrahydrofuran or dimethylsulfoxide.

Compounds of Formula V can be prepared by methods well known in the art. For example, compound V where $R^3$—$R^6$, $R^7$, and $R^9$ are hydrogen and $R^8$ and $R^{10}$ are methyl can be prepared by following the procedure described in U.S. Pat. No. 5,792,783, at column 22, lines 60–67, the disclosure of which is incorporated herein by reference. Other compounds of Formula (II) can be prepared as described in U.S. Pat. No. 5,792,783, PCT Application Publication No. WO 99/61422, and U.S. patent application Ser. No. 09/783,264, filed on Feb. 15, 2001, and titled "PYRROLE SUBSTITUTED 2-INDOLINONE AS PROTEIN KINASE INHIBITORS", the disclosures of which are hereby incorporated by reference.

Compounds of Formula II where $R^{3'}$ and $R^{4'}$ are independently alkyl or combine to form a heteroalicyclic ring may be prepared as illustrated and described below:

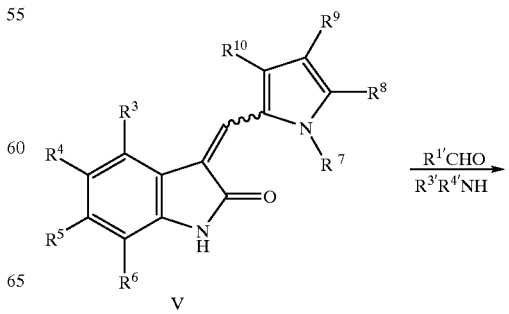

V

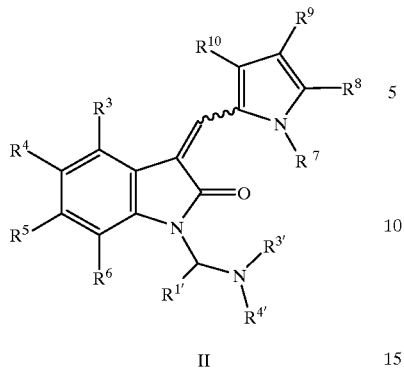

II

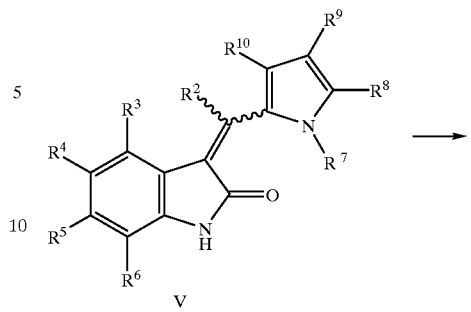

V

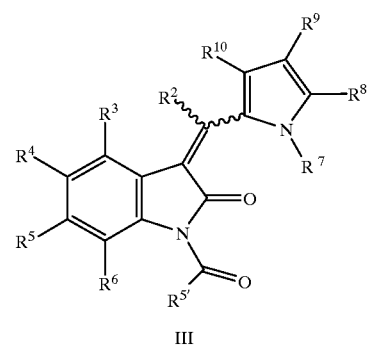

III

A compound of Formula I where $R^3$—$R^{10}$ and $R^{1'}$, $R^{3'}$ and $R^{4'}$ are as described in the Summary of the Invention can be prepared by reacting a compound of formula V with an aldehyde such as formaldehyde, acetaldehyde, and the like, and a suitable amine.

The solvent in which the reaction is carried out may be a protic or an aprotic solvent, preferably it is a protic solvent such as an alcohol e.g., methanol or ethanol, or an aqueous alcohol. The reaction may be carried out at temperatures greater than room temperature. The temperature is generally from about 20° C. to about 100° C., preferably about 40° C. to about 80° C. By "about" is meant that the temperature range is preferably within 10 degrees Celsius of the indicated temperature, more preferably within 5 degrees Celsius of the indicated temperature and, most preferably, within 2 degrees Celsius of the indicated temperature. Thus, for example, by "about 60° C." is meant 60° C.±10° C., preferably 60° C.±5° C. and most preferably, 60° C.±2° C.

Suitable amines include alicyclic and cyclic secondary amines. These amines are either commercially available from Aldrich, Sigma, etc., or they can be prepared by methods well known in the art. Exemplary secondary amines include dimethylamine, diethylamine and bis(2-hydroxyethyl)amine. Exemplary cyclic secondary amines include N-alkyl piperazine and pyrrolidine.

Compounds of formula II, where $R^{3'}$ and $R^{4'}$ combine to form a heteroaryl ring, may be prepared by reacting the parent 3-pyrrolidinyl-2-indolinone (V) with a suitable aldehyde to yield an intermediate N-hydroxyalkyl derivative of V, and reacting the intermediate with phosphorus oxychloride and a suitable heteroaryl such as pyridine.

The reaction may be carried out at temperatures less than room temperature. The temperature is generally from about −20° C. to about 20° C., preferably about −10° C. to about 10° C. By "about" is meant that the temperature range is preferably within 10 degrees Celsius of the indicated temperature, more preferably within 5 degrees Celsius of the indicated temperature and, most preferably, within 2 degrees Celsius of the indicated temperature. Thus, for example, by "about 0° C." is meant 0° C.±10° C., preferably 0° C.±5° C. and most preferably, 0° C.±2° C.

Compounds of Formula III may be prepared from a compound of Formula V as shown below:

A compound of Formula III where $R^{5'}$ is as defined in the Summary of the Invention can be readily prepared by acylating a compound of Formula V with a suitable agents e.g., carboxylic acid anhydrides such as acetic anhydride, succinic anhydride, carboxylic acid chlorides such as acetyl chloride, butryl chloride, and the like or carboxylic acid active esters. The reaction may be carried out in the presence of an organic base, preferably a tertiary nitrogen base. Examples of tertiary nitrogen bases include, but are not limited to, trimethylamine, triethylamine, pyridine, and 1,8-diazabicyclo[5.4.1]undec-7-ene.

The solvent in which the reaction is carried out may be an aprotic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydrofuran, dimethylsulfoxide, dimethylformamide and pyridine. In a presently preferred embodiment of this invention, the solvent is a polar aprotic protic solvent, preferably dimethylformamide, tetrahydrofuran or pyridine. The reaction is typically carried out at room temperature.

Compounds of Formula IV may be prepared from a compound of Formula V as shown below:

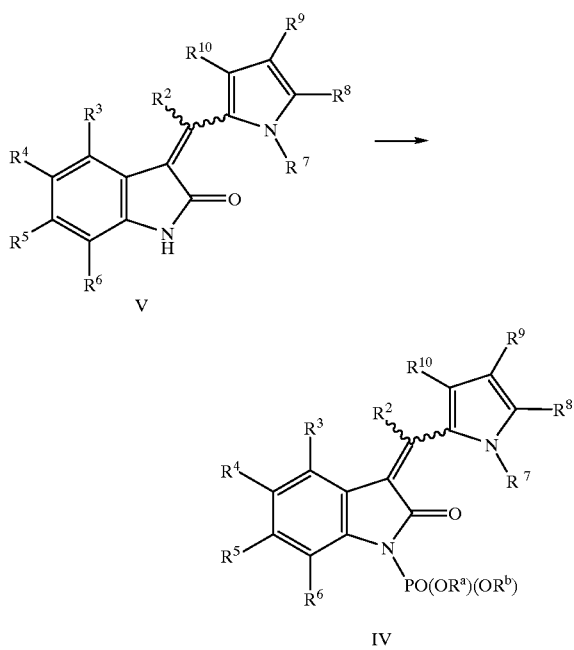

A compound of Formula IV where $R^2$—$R^{10}$ are as defined in the Summary of the Invention an $R^a$ and $R^b$ are not hydrogen can be prepared by reacting V with a phosphorylation agent such as phosphoryl halide such as dimethyl chlorophosphate. The reaction is carried out in the presence of a strong base such as sodium hydride and in an organic solvent such as THF, DMF, and the like. The methyl groups can be removed under suitable demethylation reaction conditions such as treatment with N,O-Bis(trimethylsilyl) acetamide in the presence of trimetylsilylbromide. The reaction is carried out in a polar organic solvent such as acetonitrile.

The preparation of compounds of Formula I–IV may further include the step of removing a protecting group. "Protecting group" refers to a group used to render a reactive moiety inert until removal of the group. Reactive moieties are well known to the skilled artisan; preferred reactive moieties include reactive nitrogen, oxygen, sulfur, carboxyl and carbonyl groups. Exemplary nitrogen protecting groups include, but are not limited to, benzyl, benzyloxycarbonyl, tert-butoxycarbonyl, silyl groups (e.g., tert-butyldimethylsilyl), 9-fluorenylmethoxycarbonyl, 9-phenyl-9-fluorenyl and arylsulfonyl groups (e.g., toluenesulfonyl). Exemplary oxygen protecting groups include, but are not limited to, allyloxycarbonyl, benzoyl, benzyl, tert-butyl, silyl groups (e.g., tert-butyldimethylsilyl), 2-ethoxyethyl, p-methoxybenzyl, methoxymethyl, pivaloyl, tetrahydropyran-2-yl and trityl. Exemplary carboxyl protecting groups include, without limitation, methyl, allyl, benzyl, silyl groups (e.g., tert-butyldimethylsilyl) and p-nitrobenzyl. Exemplary carbonyl protecting groups include, but are not limited to, acetyl groups (e.g., O,O-acetals).

Protecting groups may be removed using methods known in the literature. For example, for the removal of nitrogen protecting groups see Greene et al. (1991) *Protecting Groups in Organic Synthesis,* 2nd ed., John Wiley & Sons, New York, pp. 309–405 and Kocienski (1994) *Protecting Groups,* Thieme, New York, pp. 185–243. Methods for the removal of particular protecting groups are exemplified herein.

Utility

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction, is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, Neuron 9:303–391.

It has been shown that tyrosine phosphorylation sites on growth factor receptors function as high-affinity binding sites for SH2 (src homology) domains of signaling molecules. Fantl et al., 1992, Cell 69:413–423, Songyang et al., 1994, Mol. Cell. Biol. 14:2777–2785), Songyang et al., 1993, Cell 72:767–778, and Koch et al., 1991, Science 252:668–678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, Cell 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, Cell 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

In another aspect, the protein kinase, the catalytic activity of which is modulated by contact with a compound of this invention, is a protein tyrosine kinase, more particularly, a receptor protein tyrosine kinase. Among the receptor protein tyrosine kinases whose catalytic activity can be modulated with a compound of this invention, or salt thereof, are, without limitation, EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R.

The protein tyrosine kinase whose catalytic activity is modulated by contact with a compound of this invention, or a salt thereof, can also be a non-receptor or cellular protein tyrosine kinase (CTK). Thus, the catalytic activity of CTKs such as, without limitation, Src, Frk, Btk, Csk, Abl, ZAP70, Fes, Fps, Fak, Jak, Ack, Yes, Fyn, Lyn, Lck, Blk, Hck, Fgr and Yrk, may be modulated by contact with a compound or salt of this invention.

Still another group of PKs which may have their catalytic activity modulated by contact with a compound of this invention are the serine-threonine protein kinases such as, without limitation, CDK2 and Raf.

In another aspect, this invention relates to a method for treating or preventing a PK related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a PK related disorder.

This invention is therefore directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreatic cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders, metabolic disorders and infectious diseases.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-1) receptor (Shibuya et al., 1990, Oncogene,5:519–524; De Vries et al., 1992, Science, 255:989–991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, Biochem. Biophys. Res. Comm., 161:851–858; Vaisman et al., 1990, J. Biol. Chem., 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsbum & Soker, 1993, Current Biology, 3(10)699–702; Houck, et al., 1992, J. Biol. Chem., 267:26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, J. Biological Chem., 267(16):10931–34. Uncontrolled vasculogenesis and/or angiogenesis has been associated with diseases such as diabetes as well as with malignant solid tumors that rely on vascularization for growth. Klagsbum & Soker, 1993, Current Biology, 3(10):699–702; Folkham, 1991, J. Natl. Cancer Inst., 82:4–6; Weidner, et al., 1991, New Engl. J. Med., 324:1–5.

As presently understood, the role of VEGF in endothelial cell proliferation and migration during angiogenesis and vasculogenesis indicates an important role for the KDR/FLK-1 receptor in these processes. Diseases such as diabetes mellitus (Folkman, 198, in XIth Congress of Thrombosis and Haemostasis (Verstraeta, et al., eds.), pp. 583–596, Leuven University Press, Leuven) and arthritis, as well as malignant tumor growth may result from uncontrolled angiogenesis. See e.g., Folkman, 1971, N. Engl. J. Med., 285:1182–1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, DN&P, 7(6):334–339. More particularly, the KDR/FLK-1 receptor's highly specific role in neovascularization make it a choice target for therapeutic approaches to the treatment of cancer and other diseases which involve the uncontrolled formation of blood vessels.

Thus, one aspect of the present invention relates to compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, Cell, 72:835–846; Quinn et al., 1993, Proc. Natl. Acad. Sci. USA, 90:7533–7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, in one aspect, this invention is directed to compounds that regulate, modulate and/or inhibit vasculogenesis and/or angiogenesis by affecting the enzymatic activity of the KDR/FLK-1 receptor and interfering with the signal transduced by KDR/FLK-1. In another aspect, the present invention is directed to compounds which regulate, modulate and/or inhibit the KDR/FLK-1 mediated signal transduction pathway as a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggest the administration of compounds which inhibit the KDR/Flk-1 mediated signal transduction pathway may also be used in the treatment of hemangioma, restenois and diabetic retinopathy.

A further aspect of this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signaling molecules that facilitate the appropriate cellular response, e.g., cell division and metabolic effects to the extracellular microenvironment. See, Schlessinger and Ullrich, 1992, Neuron, 9:1–20.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, Proc. Natl. Acad. Sci. USA, 90:7696–7700), phosphatidylinositol-3'-kinase (Hu et al., 1992, Mol. Cell. Biol., 12:981–990), phospholipase cγ (Kashishian & Cooper, 1993, Mol. Cell. Biol., 4:49–51), ras-GTPase-activating protein, (Kashishian et al., 1992, EMBO J., 11:1373–1382), PTP-ID/syp (Kazlauskas et al., 1993, Proc. Natl. Acad. Sci. USA, 10 90:6939–6943), Grb2 (Arvidsson et al., 1994, Mol. Cell. Biol., 14:6715–6726), and the adapter molecules Shc and Nck (Nishimura et al., 1993, Mol. Cell. Biol., 13:6889–6896), have been shown to bind to regions involving different autophosphorylation sites. See generally, Claesson-Welsh, 1994, Prog. Growth Factor Res., 5:37–54. Thus, it is likely that signal transduction pathways activated by KDR/FLK-1 include the ras pathway (Rozakis et al., 1992, Nature, 360:689–692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, Kidney International 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, Br. J. Cancer 63:227–233, Torp et al., 1992, APMIS 100:713–719) HER2/neu (Slamon et al., 1989, Science 244:707–712) and PDGF-R (Kumabe et al., 1992, Oncogene, 7:627–633) are over-expressed in many tumors and/or persistently activated by autocrine loops. In fact, in the most common and severe cancers these receptor over-expressions (Akbasak and Suner-Akbasak et al., 1992, J. Neurol. Sci., 111:119–133, Dickson et al., 1992, Cancer Treatment Res. 61:249–273, Korc et al., 1992, J. Clin. Invest. 90:1352–1360) and autocrine loops (Lee and Donoghue, 1992, J. Cell. Biol., 118:1057–1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreatic and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, J. Clin. Invest. 84:1418–1423) and small lung tumor cells (Macauley et al., 1990, Cancer Res., 50:2511–2517). In addition, IGF-I, while integrally involved in the normal growth and differentiation of the nervous system, also appears to be an autocrine stimulator of human gliomas. Sandberg-Nordqvist et al., 1993, Cancer Res. 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, Eukaryotic Gene Expression,1 :301–326. In a series of recent publications, Baserga suggests that IGF-IR plays a central role in the mechanism of transformation and, as such, could be a preferred target for therapeutic interventions for a broad spectrum of human malignancies. Baserga, 1995, Cancer Res., 55:249–252, Baserga, 1994, Cell 79:927–930, Coppola et al., 1994, Mol. Cell. Biol., 14:4588–4595.

STKs have been implicated in many types of cancer including, notably, breast cancer (Cance, et al., Int. J. Cancer, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, DN&P 7:334–339.

As noted previously, CTKs including, but not limited to, src, abl, fps, yes, fyn, lyn, Ick, blk, hck, fgr and yrk (reviewed by Bolen et al., 1992, FASEB J., 6:3403–3409), are also involved in the proliferative and metabolic signal transduction pathway and thus could be expected, and have been shown, to be involved in many PTK-mediated disorders to which the present invention is directed. For example, mutated src (v-src) has been shown to be an oncoprotein (pp60$^{v\text{-}src}$) in chicken. Moreover, its cellular homolog, the proto-oncogene pp60$^{c\text{-}src}$ transmits oncogenic signals of many receptors. Over-expression of EGFR or HER2/neu in tumors leads to the constitutive activation of pp60$^{c\text{-}src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

In yet another aspect, the compounds of the instant invention can also be used as anti-infective agents. For example, indolinone compounds are known to exhibit antibacterial and antifungal activities. See, e.g., Singh and Jha (1989) "Indolinone derivatives as potential antimicrobial agents," Zentralbl. Mikrobiol. 144(2):105–109. In addition, indolinone compounds have been reported to exhibit significant antiviral activity. See, e.g., Maass et al. (1993) "Viral resistance to the thiazolo-iso-indolinones, a new class of nonnucleoside inhibitors of human immunodeficiency virus type 1 reverse transcriptase," Antimicrob. Agents Chemother. 37(12):2612–2617.

Finally, both RTKs and CTKs are currently suspected as being involved in hyperimmune disorders.

A method for identifying a chemical compound that modulates the catalytic activity of one or more of the above discussed protein kinases is another aspect of this invention. The method involves contacting cells expressing the desired protein kinase with a compound of this invention (or its salt) and monitoring the cells for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of the protein kinase in the cells or a change or absence of change in the interaction of the protein kinase with a natural binding partner.

Pharmaceutical Compositions and Administration

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

As used herein, "administer" or "administration" refers to the delivery of a compound or salt of the present invention or of a pharmaceutical composition containing a compound or salt of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water with or without additional surfactants or cosolvents such as polysorbate 80, Cremophor, cyclodextrin sulfobutyl ether, propylene glycol, or polyethylene glycol such as PEG-300 or PEG-400, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80™, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, citrate, mesylate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)$_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated. Therapeutically effective amounts of compounds of Formula I–IV may range from approximately 10 mg/m$^2$ to 400 mg/m$^2$, preferably 50 mg/m$^2$ to 300 mg/m$^2$, more preferably 100 mg/m$^2$ to 220 mg/m$^2$, even more preferably 195 mg/m$^2$. For any compound used in the methods of the invention, the therapeutically effective amount or dose can be estimated initially from cell culture assays. Then, the dosage can be formulated for use in animal models so as to achieve a circulating concentration range that includes the IC$_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the IC$_{50}$ and the LD$_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Preferably, the Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%. In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormnone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole).

Finally, the combination of a compound of this invention might be expected to be particularly effective in combination with CAMPTOSAR™, GLEEVEC™, HERCEPTIN™, ENDOSTATIN™, Cox-2 inhibitors, MITOXANTRONE™ or PACLITAXEL™ for the treatment of solid tumor cancers or leukemias such as, without limitation, acute myelogenous (non-lymphocytic) leukemia.

EXAMPLES

The following preparations and examples are given to enable those skilled in the art to more clearly understand and to practice the present invention. They should not be considered as limiting the scope of the invention, but merely as being illustrative and representative thereof.

In general HPLC data was obtained with a Zorbax SB C18 column (4.6 mm ID×7.5 cm), a Perkin Elmer series 200 pump programmed to run from 10% acetonitrile/water 0.1% TFA (solvent A) to 90% acetonitrile/water (solvent B) with a flow rate of 1.5 mL/min. After 0.1 min on solvent A, a 5 min linear program to solvent B was run, followed by 3 min on solvent B, before recycling to solvent A (2 min). Detection was with a Perkin Elmer diode array detector recording at 215 and 280 nM). NMR spectra were recorded on a Bruker instrument at 300 MHz.

Synthetic Examples
A. Oxymethyl Substituted Indolinones (I)

Example 1

Synthesis of (3Z)-3-[(3,5-dimethyl-1H-pyrrol-2-yl)-methylidene]-1-(hydroxymethyl)-1,3-dihydro-2H-indol-2-one (1)

Aqueous formaldehyde (15.0 g of 38% solution, 190 mmol) was added to a stirred solution of 3-(3,5-dimethyl-1H-pyrrol-2-ylmethylidene)-1,3-dihydro-indol-2-one (23.8 g, 100 mmol) and triethylamine (15.0 g, 150 mmol) in dimethylformamide (200 mL). After 1 h, the solution was diluted with water and the precipitate was filtered off, washed with water, and dried to give 26.4 g of the title compound, mp 196–200° C. HPLC Rt 5.71 min. $^1$H NMR (CDCl$_3$) δ2.34 (s, 6H), 3.14 (t, 1H), 5.44 (d, 2H), 5.98 (d, 1H), 7.08 (m, 2H), 7.18 (m, 1H), 7.36 (s, 1H), 7.48 (dd, 1H) and 13.0 (br s, 1H). Anal. Calcd for $C_{16}H_{16}N_2O_2$: C, 71.62; H, 6.01; N, 10.44. Found: C, 71.33; H, 6.09; N, 10.43. A sample was recrystallized from ethyl acetate; mp 200–202° C.

Example 2

Synthesis of {3(Z)-3-[(3,5-dimethyl-1H-pyrrol-2-yl)-methylidene]-2-oxo-2,3-dihydro-1H-indol-1-yl}methyl acetate (2)

Acetic anhydride (5.0 mL, 50 mmol) was added to a stirred solution of (3Z)-3-[(3,5-dimethyl-1H-pyrrol-2-yl)-methylidene]-1-(hydroxymethyl)-1,3-dihydro-2H-indol-2-one (1) (2.68 g, 10 mmol) in pyridine (30 mL). HPLC showed that acetylation was complete in 1 h, at which time the solution was diluted with water (80 mL). The precipitate was filtered off, washed with water, and dried to give 2.94 g of the title compound, mp 145–152° C. The product was recrystallized from methanol to give 2.75 g, mp 150–152° C. HPLC Rt 6.58 min. $^1$H NMR (CDCl$_3$) δ2.09 (s, 3H), 2.33 (s, 3H), 2.38 (s, 3H), 5.94 (s, 2H), 5.99 (d, 1H), 7.10 (m, 2H), 7.20 (m, 1H), 7.39 (s, 1H), 7.50 (dd, 1H) and 13.0 (br s, 1H). Anal. Calcd for $C_{18}H_{18}N_2O_3$: C, 69.66; H, 5.85; N, 9.03. Found: C, 69.57; H, 5.85; N, 9.06.

Example 3

Synthesis of 4-({(3Z)-3-[(3,5-dimethyl-1H-pyrrol-2-yl)-methylidene]-2-oxo-2,3-dihydro-1H-indol-1-yl}methoxy)-4-oxobutanoic acid (3)

Succinic anhydride (5.0 g, 50 mmol) was added to a stirred solution of (3Z)-3-[(3,5-dimethyl-1H-pyrrol-2-yl)-methylidene]-1-(hydroxymethyl)-1,3-dihydro-2H-indol-2-one (1) (2.68 g, 10 mmol) in pyridine (30 mL). HPLC showed that the reaction was 90% complete after 18 h. At this time, the solution was cooled to −10° C., the precipitate was filtered off, washed with aqueous pyridine and then with water, and was dried to give 3.57 g of the pyridinium salt of the title compound, mp 200–202° C. HPLC Rt 5.85 min. $^1$H NMR (CDCl$_3$) δ2.35 (s, 3H), 2.40 (s, 3H), 2.70 (s, 4H), 6.01 (s, 3H), 7.10 (m, 2H), 7.18 (m, 1H), 7.43 (s, 1H), 7.50 (m, 3H), 7.93, (m, 1H), 8.68 (m, 1 H). HPLC Rt 5.85 min. $^1$H NMR [(CD$_3$)$_2$SO] δ2.33 (s, 3H), 2.36 (s, 3H), 2.50 (m, 4H), 5.91 (s, 2H), 6.07 (d, 1H), 7.15 (m, 3H), 7.40 (m, 2H), 7.67 (s, 1H), 7.80 (m, 2H), 8.58, (dd, 1H), 12.2 (s, 1 H), and 13.1 (s, 1H). Anal. Calcd for $C_{20}H_{20}N_2O_5 \cdot C_5H_5N$: C, 67.10; H, 5.63; N, 9.39. Found: C, 67.11; H, 5.70; N, 9.42.

Hydrochloric acid solution (20 mL of 1.0 N) was added to a stirred solution of the above salt (2.94 g) in tetrahydrofuran (25 mL). Water (100 mL) was added and the precipitate of product was filtered off and dried to give 2.38 g of the title compound, mp 160–163° C. The bulk of the product was recrystallized from ethyl acetate to give 2.08 g, mp 160–162° C. HPLC Rt 5.85 min. $^1$H NMR (CDCl$_3$) δ2.32 (s, 3H), 2.37 (s, 3H), 2.66 (s, 4H), 6.01 (s, 3H), 7.05–7.25 (m, 3H), 7.40 (s, 1H), 7.49 (dd, 1H), and 13.0 s, 1H). $^1$H NMR [(CD$_3$)$_2$SO] δ2.32 (s, 3H), 2.35 (s, 3H), 2.52 (m, 4H), 5.90 (s, 2H), 6.06 (d, 1H), 7.05–7.25 (m, 3H), 7.64 (s, 1H), 7.80 (dd, 1H), 12.2 (s, 1 H), and 13.1 (s, 1H). Anal. Calcd for C$_{20}$H$_{20}$N$_2$O$_5$: C, 65.21; H, 5.47; N, 7.60. Found: C, 65.14; H, 5.49; N, 7.60.

Example 4

Synthesis of 1-{(3Z)-3-[(3,5-dimethyl-1H-pyrrol-2-yl)-methylidene]-2-oxo-2,3-dihydro-1H-indol-1-yl}ethyl acetate (4a)

A mixture of acetic anhydride (2.1 g, 20 mmol), acetaldehyde (4.4 g, 100 mmol), triethylamine (2.0 g, 20 mmol) and 3-(3,5-dimethyl-1H-pyrrol-2-ylmethylidene)-1,3-dihydro-indol-2-one (2.38 g, 10 mmol) in DMF (30 mL) was stirred at room temperature for 3 days. The solvents were removed and the residual oil was chromatographed on silica gel to give, as the first product eluted from the column, 2.5 g of product, which was crystallized from ether to give 2.1 g of the title compound, mp 107–110° C. HPLC Rt 6.78 min. $^1$H NMR (CDCl$_3$) δ1.81 (d, 3H), 2.09 (s, 3H), 2.33 (s, 3H), 2.38 (s, 3H), 5.98 (s, 2H), 7.00–7.20 (m, 3H), 7.25 (dd, 1H), 7.39 (s, 1H), 7.51 (dd, 1H) and 13.0 (br s, 1 H). Anal. Calcd for C$_{19}$H$_{20}$N$_2$O$_3$: C, 70.35; H, 6.21; N, 8.64. Found: C, 70.33; H, 6.18; N, 8.60.

Continued elution of the column gave 0.2 g of (3Z)-3-[(3,5-dimethyl-1H-pyrrol-2-yl)methylidene]-1-(1-hydroxyethyl)-1,3-dihydro-2H-indol-2-one (4b), mp 145 (dec). $^1$H NMR (CDCl$_3$) δ1.76 (d, 3H), 2.33 (s, 3H), 2.38 (s, 3H), 3.71 (br s, 1H), 5.98 (d, 2H), 6.15 (q, 1H), 7.00–7.25 (m, 3H), 7.34 (s, 1H), 7.47 (dd, 1H) and 13.0 (br s, 1H). Anal. Calcd for C$_{17}$H$_{18}$N$_2$O$_2$: C, 72.32; H, 6.43; N, 9.92. Found: C, 72.22; H, 6.52; N, 9.79.

Alternatively, (3Z)-3-[(3,5-dimethyl-1H-pyrrol-2-yl)methylidene]-1-(1-hydroxyethyl)-1,3-dihydro-2H-indol-2-one (4b) was prepared in >90% yield by treating 1-{(3Z)-3-[(3,5-dimethyl-1H-pyrrol-2-yl)-methylidene]-2-oxo-2,3-dihydro-1H-indol-1-yl}ethyl acetate (4a) (500 mg) with aqueous acetonitrile (10 mL) and formic acid (200 mg) overnight.

Example 5

Synthesis of 3-[5-{(Z)-[1-(hydroxymethyl)-1,2-dihydro-3H-indol-3-ylidine]methyl}-2,4-dimethyl-1H-pyrrole-3-propanoic acid (5)

Aqueous formaldehyde (500 mg of 38% solution, 5 mmol) was added to a stirred solution of 3-[5-{(Z)-[1,2-dihydro-3H-indol-3-ylidine]methyl}-2,4-dimethyl-1H-pyrrole-3-propanoic acid (310 mg, 1 mmol) and triethylamine (200 mg, 2 mmol) in dimethylformamide (3 mL). After 1 h, the solution was diluted with 1 N hydrochloric acid (5 mL) and the precipitate was filtered off, washed with water, and dried to give 210 mg of the title compound. HPLC Rt 5.91 min. $^1$H NMR [(CD$_3$)$_2$SO] δ2.27 (s, 3H), 2.32 (s, 3H), 2.36 (t, 2), 2.65 (t,2H), 5.25 (d, 2), 6.26 (t, 1H), 7.05 (m, 1H), 7.15 (m, 2H), 7.62 (s, 1H), 7.79 (d, 1H), 12.0 (br s, 1H) and 13.3 (br s, 1H).

Example 6

Synthesis of dibenzyl {(3Z)-3-[(3,5-dimethyl-1H-pyrrol-2-yl)methylidene]-2-oxo-2,3-dihydro-1H-indol-1-yl)}methyl phosphate (6)

The title compound was prepared from (3Z)-3-[(3,5-dimethyl-1H-pyrrol-2-yl)-methylidene]-1-(hydroxymethyl)-1,3-dihydro-2H-indol-2-one (1) and dibenzyl phosphorochloridate (modification of procedure used to prepare {3(Z)-3-[(3,5-dimethyl-1H-pyrrol-2-yl)-methylidene]-2-oxo-2,3-dihydro-1H-indol-1-yl}methyl acetate (2)).

Example 7

Synthesis of {(3Z)-3-[(3,5-dimethyl-1H-pyrrol-2-yl)methylidene]-2-oxo-2,3-dihydro-1H-indol-1-yl}methyl dihydrogen phosphate (7)

The title compound was prepared by hydrogenation of dibenzyl {(3Z)-3-[(3,5-dimethyl-1H-pyrrol-2-yl)methylidene]-2-oxo-2,3-dihydro-1H-indol-1-yl}methyl phosphate (6) (modification of procedure used to prepare (3Z)-1-(aminoacetyl)-3-{[3,5-dimethyl-4-(2-carboxyethyl)-1H-pyrrol-2-yl]-methylidene}-1,3-dihydro-2H-indol-2-one (20) vide infra).

Example 8

Synthesis of benzyl {(3Z)-3-[(3,5-dimethyl-1H-pyrrol-2-yl)methylidene]-2-oxo-2,3-dihydro-1H-indol-1-yl}methyl methyl phosphate (8)

The title compound was prepared from (3Z)-3-[(3,5-Dimethyl-1H-pyrrol-2-yl)-methylidene]-1-(hydroxymethyl)-1,3-dihydro-2H-indol-2-one (1) and benzyl methyl phosphorochloridate (modification of procedure used to prepare {3(Z)-3-[(3,5-dimethyl-1H-pyrrol-2-yl)-methylidene]-2-oxo-2,3-dihydro-1H-indol-1-yl}methyl acetate (2)).

Example 9

Synthesis of {(3Z)-3-[(3,5-dimethyl-1H-pyrrol-2-yl)methylidene]-2-oxo-2,3-dihydro-1H-indol-1-yl}methyl methyl hydrogen phosphate (9)

The title compounded was prepared by hydrogenation of benzyl {(3Z)-3-[(3,5-dimethyl-1H-pyrrol-2-yl)methylidene]-2-oxo-2,3-dihydro-1H-indol-1-yl}methyl methyl phosphate (8) (modification of procedure used to prepare (3Z)-1-(aminoacetyl)-3-{[3,5-dimethyl-4-(2-carboxyethyl)-1H-pyrrol-2-yl]-methylidene}-1,3-dihydro-2H-indol-2-one (20) vide infra).

Example 10

Synthesis of {(3Z)-3-[(3,5-dimethyl-1H-pyrrol-2-yl)methylidene]-2-oxo-2,3-dihydro-1H-indol-1-yl}methyl(dimethylamino)acetate (10)

Following the procedure of Example 2, the title compound was prepared from 2-chloro-N,N-dimethyl-2-oxoethanaminium chloride and (3Z)-3-[(3,5-dimethyl-1H-pyrrol-2-yl)-methylidene]-1-(hydroxymethyl)-1,3-dihydro-2H-indol-2-one (1).

Example 11

Synthesis of 2-({(3Z)-3-[(3,5-dimethyl-1H-pyrrol-2-yl)methylidene]-2-oxo-2,3-dihydro-1H-indol-1-yl}methoxy)-N,N,N-trimethyl-2-oxoethanaminium chloride (11)

Following the procedure of Example 2, the title compound was prepared from 2-chloro-N,N,N-trimethyl-2-oxoethanaminium chloride and (3Z)-3-[(3,5-dimethyl-1H- pyrrol-2-yl)-methylidene]-1-(hydroxymethyl)-1,3-dihydro-2H-indol-2-one (1).

B. Aminomethyl Substituted Indolinones (II)

Example 12

Synthesis of 1-({(3Z)-3-[(3,5-dimethyl-1H-pyrrol-2-yl)-methylidene]-2-oxo-1,3-dihydro-1H-indol-1-yl}methyl)pyridinium chloride (12)

Phosphorus oxychloride (3.1 g, 10 mmol) was added at 0° C. to a stirred solution of (3Z)-3-[(3,5-dimethyl-1H-pyrrol-2-yl)-methylidene]-1-(hydroxymethyl)-1,3-dihydro-2H-indol-2-one (1). (2.68 g, 10 mmol) in pyridine (20 mL). After 130 min, the solution was diluted slowly with water (20 mL) and the precipitate was filtered off, washed with water, and dried to give 3.3 g of the title compound, mp >280° C. HPLC Rt 4.78 min. $^1$H NMR [(CD$_3$OD] δ2.35 (s, 3H), 2.37 (s, 3H), 6.07 (d, 1H), 6.71 (s, 2H), 7.12–7.32 (m, 3H), 7.62 (s, 1H), 7.68 (dd, 1H), 8.17, (m, 2H), 8.67 (m, 1H), 9.3 (d, 1H), and 13.1 (br s, 1H). Anal. Calcd for C$_{21}$H$_{20}$ClN$_3$O: C, 68.94; H, 5.51; Cl, 9.69; N, 11.48. Found: C, 68.63; H, 5.53; Cl, 9.53; N, 11.45.

Example 13

Synthesis of (3Z)-3-[(3,5-dimethyl-1H-pyrrol-2-yl)-methylidene]-1-[1-(4-methylpiperazinyl)methyl]-1,3-dihydro-2H-indol-2-one (13)

N-Methylpiperazine (10 g, 100 mmol) was added to a stirred solution of aqueous formaldehyde (10 g of 38% solution, 100 mmol) and 3-(3,5-dimethyl-1H-pyrrol-2-ylmethylene)-1,3-dihydro-indol-2-one, (2.38 g, 10 mmol) in methanol (100 mL). The solution heated at 60° C. for 1 h, concentrated to a low volume and the precipitate was filtered off, washed with methanol, and dried to give 2.38 g of the title compound, mp 160–164° C. HPLC Rt 4.72 min. $^1$H NMR (CDCl$_3$) δ2.26 (s, 3H), 2.33 (s, 3H), 2.38 (s, 3H), 2.43 (br s, 4H), 2.70 (br s, 4 H), 4.59 (s, 2H), 5.96 (d, 1H), 7.02–7.08 (m, 2H), 7.15 dd, 1H), 7.38 (s, 1H), 7.48 (dd, 1H) and 13.0 (br s, 1H). Anal. Calcd for C$_{21}$H$_{26}$N$_4$O: C, 71.97; H, 7.48; N, 15.99. Found: C, 71.75; H, 7.46; N, 15.87.

(3Z)-3-[(3,5-Dimethyl-1H-pyrrol-2-yl)-methylidene]-1-[1-(4-methylpiperazinyl)-methyl]-1,3-dihydro-2H-indol-2-one (13) has been converted to a dihydrochloride salt.

Example 14

Synthesis of (3Z)-3-[(3,5-dimethyl-1H-pyrrol-2-yl)-methylidene]-1-(1-pyrrolidinylmethyl)-1,3-dihydro-2H-indol-2-one (14)

Pyrrolidine (450 mg, 6.3 mmol) was added to a stirred solution of aqueous formaldehyde (500 mg of 38% solution, 6.0 mmol) and 3-(3,5-dimethyl-1H-pyrrol-2-ylmethylene)-1,3-dihydro-indol-2-one, (900 mg, 3.8 mmol) in methanol (50 mL). After 15 min, the solution was cooled to 0° C. and the precipitate was filtered off, washed with water, and dried to give 1.08 g of the title compound, mp 129–132° C. HPLC Rt 4.87 min. $^1$H NMR [(CD$_3$)$_2$SO] δ1.65 (m, 4H), 2.32 9s, 3H), 2.34 (s, 3H), 2.62 (m, 4H). 4.72 (s, 2H) 6.07 (d, 1H), 7.00 (m, 1H), 7.15 (m, 2H), 7.61 (s, 1H), 7.76 (d, 2H) and 13.1 (br s, 1H). Anal. Calcd for C$_{20}$H$_{23}$N$_3$O: C, 74.74; H, 7.21; N, 13.07. Found: C, 74.61; H, 7.25; N, 13.03.

C. Acyl Substituted Indolinones (III)

Example 15

Synthesis of (3Z)-1-Acetyl-3-[(3,5-dimethyl-4-1H-pyrrol-2-yl)-methylidene]-1,3-dihydro-2H-indol-2-one (15)

The title compound was prepared according to Procedure 1 or Procedure 2.

Procedure 1: Sodium hydride (200 mg of 60% in oil) was added to a stirred solution of 3-(3,5-dimethyl-1H-pyrrol-2-ylmethylidene)-1,3-dihydro-indol-2-one (1.19 g, 5 mmol) in DMF (30 mL). After 10 min, acetic anhydride (1.02 g, 10 mmol) in DMF (10 mL) was added. Water (80 mL) was added to complete precipitation of the product. The dried product was chromatographed on silica gel with chloroform as the eluant to give 1.05 g of the title compound which was triturated with ether; mp 193–196° C. HPLC Rt 6.98 min. $^1$H NMR (CDCl$_3$) δ2.34 (s, 3H), 2.42 (s, 3H), 2.79 (s, 3H), 6.06 (d, 1H), 7.19 (m, 2H), 7.38 (s, 1H), 7.42 (m, 1H), 8.24 (m, 1H) and 12.6 (br s, 1H). Anal. Calcd for C$_{17}$H$_{16}$N$_2$O$_2$: C, 72.84; H, 5.75; N, 9.99. Found: C, 72.55; H, 5.50; N, 9.86.

Procedure 2: A mixture of 3-(3,5-dimethyl-1H-pyrrol-2-ylmethylidene)-1,3-dihydro-indol-2-one (930 mg, 3.9 mmol) and acetic anhydride (15 mL, excess) was heated at 95° C. for several days. TLC showed no SM. The reaction was cooled to room temperature and the resulting precipitate was collected by vacuum filtration, washed with water and dried to give 1.03 g (94%) of the title compound. $^1$HNMR (300 MHz, DMSO-d6) δ12.54 (v br s, 1H, NH), 8.10 (m, 1H), 7.85 (m, 1H), 7.64 (s, 1H, H-vinyl), 7.2 (m, 2H), 6.12 (d, J=2.4 Hz, 1H), 2.70 (s, 3H, COCH$_3$), 2.38 (s, 3H, CH$_3$), 2.34 (s, 3H, CH$_3$). MS MH$^+$ 281.2.

Example 16

Synthesis of (3Z)-1-[(Dimethylamino)acetyl]-3-[(3,5-dimethyl-4-1H-pyrrol-2-yl)-methylidene]-1,3-dihydro-2H-indol-2-one (16)

The title compound was prepared from 3-(3,5-dimethyl-1H-pyrrol-2-ylmethylidene)-1,3-dihydro-indol-2-one and 2-chloro-N,N-dimethyl-2-oxoethanaminium chloride (modification of procedure used to prepare (3Z)-1-acetyl-3-[(3,5-dimethyl-4-1H-pyrrol-2-yl)-methylidene]-1,3-dihydro-2H-indol-2-one (15)).

Example 17

Synthesis of 2-{(3Z)-3-[(3,5-dimethyl-1H-pyrrol-2-yl)-methylidene]-2-oxo-2,3-dihydro-1H-indol-1-yl}-N,N,N-trimethyl-2-oxo-1-ethanaminium chloride (17)

The title compound was prepared from 3-(3,5-dimethyl-1H-pyrrol-2-ylmethylidene)-1,3-dihydro-indol-2-one and 2-chloro-N,N,N-trimethyl-2-oxoethanaminium chloride (modification of procedure used to prepare (3Z)-1-acetyl-3-[(3,5-dimethyl-4-1H-pyrrol-2-yl)-methylidene]-1,3-dihydro-2H-indol-2-one (15)).

Example 18

Synthesis of 4-{(3Z)-3-[(3,5-dimethyl-1H-pyrrol-2-yl)-methylidene]-2-oxo-2,3-dihydro-1H-indol-1-yl}-4-oxobutanoic acid (18)

The title compound was prepared from 3-(3,5-dimethyl-1H-pyrrol-2-ylmethylidene)-1,3-dihydro-indol-2-one and succinic anhydride (modification of procedure used to prepare (3Z)-1-acetyl-3-[(3,5-dimethyl-4-1H-pyrrol-2-yl)-methylidene]-1,3-dihydro-2H-indol-2-one (15)).

Example 19

Synthesis of benzyl 2-{(3Z)-3-[(3,5-dimethyl-1H-pyrrol-2-yl)methylidene]-2-oxo-2,3-dihydro-1H-indol-1-yl}-2-oxoethylcarbamate (19)

A mixture of N-(benzyloxycarbonyl)glycine (4.9 g, 23 mmol), 3-(3,5-dimethyl-1H-pyrrol-2-ylmethylidene)-1,3- dihydro-indol-2-one (2.38 g, 10 mmol), dimethylaminopyridine (1.28 g, 10 mmol) in DMF (20 mL) was heated at 55° C. for 2 h. The solution was cooled, ether (10 mL) was added and the precipitate of the title compound was filtered off and dried to give 2.35 g, mp 193–196° C. HPLC Rt 7.04 min. $^1$H NMR (CDCl$_3$) δ2.34 (s, 3H), 2.42 (s, 3H), 4.87 (d, 2H), 5.18 (s, 2H), 5.74 (t, 1H), 6.06 (d, 1H), 7.2 (m, 3H), 7.3–7–65 (m, 7H), 7.49 (m, 1H), and 8.23 (m, 1H). Anal. Calcd for C$_{25}$H$_{23}$N$_3$O$_4$: C, 69.92; H, 5.40; N, 9.78. Found: C, 69.91; H, 5.50; N, 9.86.

Example 20

Synthesis of (3Z)-1-(aminoacetyl)-3-{[3,5-dimethyl-4-(2-carboxyethyl)-1H-pyrrol-2-yl]-methylidene}-1,3-dihydro-2H-indol-2-one (20)

Benzyl 2-{(3Z)-3-[(3,5-dimethyl-1H-pyrrol-2-yl)methylidene]-2-oxo-2,3-dihydro-1indol-1-yl}-2-oxoethylcarbamate (19) (160 mg) was dissolved in ethyl acetate (70 mL). 10% Palladium on carbon (200 mg) was added and the mixture was hydrogenated at 50 psi hydrogen pressure for 1 h to give the title compound in 35% yield; HPLC Rt 4.63 min.

Example 21

Synthesis of (3Z)-3-[(3,5-dimethyl-1H-pyrrol-2-yl)-methylidene]-1-(dimethylphosphoryl)-1,3-dihydro-2H-indol-2-one (21)

(3Z)-3-[(3,5-dimethyl-1H-pyrrol-2-yl)-methylidene]-1,3-dihydro-2H-indol-2-one (521 mg, 2.19 mmol) was dissolved in THF (60 ml). The reaction mixture was cooled to −78° C. Butyllithium (2.7 ml, 4.32 mmol; 1.6 M in hexane) was added dropwise followed by the dropwise addition of dimethyl chlorophosphate (0.46 ml, 4.27 mmol). The reaction mixture was stirred for 1 h at −78° C., then the mixture was allowed to warm to 0° C. during 4 h. The reaction mixture was poured into ice water and extracted with EtOAc (2×). The organic layers were washed with brine and dried over sodium sulfate. The solvent was removed and the residue was purified by silica gel chromatography (CH$_2$Cl$_2$/EtOAc: 10/1; 250 ml; CH$_2$Cl$_2$/EtOAc: 3/1; 300 ml) to yield the title compound as a red solid (87%).

$^1$H NMR (400 MHz, d$_6$-DMSO) δ2.35 (s, 3H), 2.38 (s, 3H), 3.80 (d, J=12.1 Hz, 6H), 6.12 (d, J=2.3 Hz, 1H), 7.13–7.20 (m, 2H), 7.67 (d, J=1.2 Hz, 1H), 7.71 (dd, J=2.0, 7.2 Hz, 1H), 7.84 (dd, J=2.0, 7.0 Hz, 1H), 12.64 (s, 1H); $^{31}$P NMR (162 MHz, d$_6$-DMSO) δ−1.05.

Example 22

Synthesis of (3Z)-3-[(3,5-dimethyl-1H-pyrrol-2-yl)-methylidene]-1-(phosphoryl)-1,3-dihydro-2H-indol-2-one (22)

(3Z)-3-[(3,5-Dimethyl-1H-pyrrol-2-yl)-methylidene]-1-(dimethylphosphoryl)-1,3-dihydro-2H-indol-2-one (648 mg, 1.87 mmol) was dissolved in CH$_3$CN (11 ml). N,O-bis(trimethylsilyl)acetamide (0.53 ml, 2.14 mmol) and trimetylsilylbromide (0.53 ml, 4.02 mmol) were added dropwise at rt. The dark red solution was stirred for 14 h at rt. The solution was distributed into two scintillation vials and water (0.2 ml per vial) was added. The product precipitated out. The vials were centrifuged and the solvent was decanted. The orange/red solid was washed with EtOAc (3×) to provide the title compound (94%).

$^1$H NMR (400 MHz, d$_6$-DMSO) δ2.33 (s, 3H), 2.35 (s, 3H), 6.08 (d, J=2.0 Hz, 1H), 7.05–7.15 (m, 2H), 7.61 (s, 1H), 7.78 (d, J=7.8 Hz, 1H), 7.83 (d, J=7.8 Hz, 1H), 12.99 (s, 1H); $^{31}$P NMR (162 MHz, d$_6$-DMSO) δ−6.98.

Biological Evaluation

It will be appreciated that, in any given series of compounds, a range of biological activities will be observed. In its presently preferred embodiments, this invention relates to novel 1-substituted-3-pyrrolidinyl-2-indolinones capable of generating in vivo 3-pyrrolidinyl-2-indolinones capable of modulating, regulating and/or inhibiting protein kinase activity. The following assays may be employed to select those compounds demonstrating the optimal degree of the desired activity.

Assay Procedures

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The presently preferred protocols for conducting the ELISA experiments for specific PKs is provided below. However, adaptation of these protocols for determining the activity of compounds against other RTKs, as well as for CTKs and STKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or H$^3$-thymidine is added. The amount of labeled DNA is detected with either an anti-BrdU antibody or by measuring radioactivity and is compared to control cells not contacted with a test compound.

GST-Flk-1 Bioassay

This assay analyzes the tyrosine kinase activity of GST-Flk1 on poly(glu-tyr) peptides.

Materials and Reagents

1. Corning 96-well ELISA plates (Corning Catalog No. 25805-96).
2. poly(glu-tyr) 4:1, lyophilizate (Sigma Catalog No. P0275), 1 mg/ml in sterile PBS.
3. PBS Buffer: for 1 L, mix 0.2 g KH$_2$PO$_4$, 1.15 g Na$_2$HPO$_4$, 0.2 g KCl and 8 g NaCl in approx. 900 ml dH$_2$O. When all reagents have dissolved, adjust the pH to 7.2 with HCl. Bring total volume to 1 L with dH$_2$O.

4. PBST Buffer: to 1 L of PBS Buffer, add 1.0 ml Tween-20.
5. TBB-Blocking Buffer: for 1 L, mix 1.21 g TRIS, 8.77 g NaCl, 1 ml TWEEN-20 in approximately 900 ml dH$_2$O. Adjust pH to 7.2 with HCl. Add 10 g BSA, stir to dissolve. Bring total volume to 1 L with dH$_2$O. Filter to remove particulate matter.
6. 1% BSA in PBS: add 10 g BSA to approx. 990 ml PBS buffer, stir to dissolve. Adjust total volume to 1 L with PBS buffer, filter to remove particulate matter.
7. 50 mM Hepes pH 7.5.
8. GST-Flk1 cd purified from sf9 recombinant baculovirus transformation (SUGEN, Inc.).
9. 4% DMSO in dH$_2$O.
10. 10 mM ATP in dH$_2$O.
11. 40 mM MnCl$_2$
12. Kinase Dilution Buffer (KDB): mix 10 ml Hepes (pH 7.5), 1 ml 5M NaCl, 40 μL 100 mM sodium orthovanadate and 0.4 ml of 5% BSA in dH$_2$O with 88.56 ml dH$_2$O.
13. NUNC 96-well V bottom polypropylene plates, Applied Scientific Catalog # AS-72092
14. EDTA: mix 14.12 g ethylenediaminetetraacetic acid (EDTA) with approx. 70 ml dH$_2$O. Add 10 N NaOH until EDTA dissolves. Adjust pH to 8.0. Adjust total volume to 100 ml with dH$_2$O.
15. 1° and 2° Antibody Dilution Buffer: mix 10 ml of 5% BSA in PBS buffer with 89.5 ml TBST.
16. Anti-phosphotyrosine rabbit polyclonal antisera (SUGEN, Inc.)
17. Goat anti-rabbit HRP conjugate.
18. ABST solution: To approx. 900 ml dH$_2$O add 19.21 g citric acid and 35.49 g Na$_2$HPO$_4$. Adjust pH to 4.0 with phosphoric acid. Add 2,2'-Azinobis(3-ethyl-benzthiazoline-6-sulfonic acid (ABTS, Sigma, Cat. No. A-1888, hold for approx. ½ hour, filter.
19. 30% Hydrogen Peroxide.
20. ABST/H$_2$O$_2$: add 3 μl of H$_2$O$_2$ to 15 ml of ABST solution.
21. 0.2 M HCl.

Procedure
1. Coat Corning 96-well ELISA plates with 2 μg of polyEY in 100 μl PBS/well, hold at room temperature for 2 hours or at 4° C. overnight. Cover plates to prevent evaporation.
2. Remove unbound liquid from wells by inverting plate. Wash once with TBST. Pat the plate on a paper towel to remove excess liquid.
3. Add 100 μl of 1% BSA in PBS to each well. Incubate, with shaking, for 1 hr. at room temperature.
4. Repeat step 2.
5. Soak wells with 50 mM HEPES (pH7.5, 150 μl/well).
6. Dilute test compound with dH$_2$O/4% DMSO to 4 times the desired final assay concentration in 96-well polypropylene plates.
7. Add 25 μl diluted test compound to each well of ELISA plate. In control wells, place 25 μl of dH$_2$O/4% DMSO.
8. Dilute GST-Flk1 0.005 μg (5 ng)/well in KDB.
9. Add 50 μl of diluted enzyme to each well.
10. Add 25 μl 0.5 M EDTA to negative control wells.
11. Add 25 μl of 40 mM MnCl$_2$ with 4× ATP (2 μM) to all wells (100 μl final volume, 0.5 μM ATP final concentration in each well).
12. Incubate, with shaking, for 15 minutes at room temperature.
13. Stop reaction by adding 25 μl of 500 mM EDTA to each well.
14. Wash 3× with TBST and pat plate on paper towel to remove excess liquid.
15. Add 100 μl per well anti-phosphotyrosine antisera, 1:10,000 dilution in antibody dilution buffer. Incubate, with shaking, for 90 min. at room temperature.
16. Wash as in step 14.
17. Add 100 μl/well of goat anti-rabbit HRP conjugate (1:6,000 in antibody dilution buffer). Incubate, with shaking, for 90 minutes are room temperature.
18. Wash as in Step 14.
19. Add 100 μl room temperature ABST/H$_2$O$_2$ solution to each well.
20. Incubate, with shaking for 15 to 30 minutes at room temperature.
21. If necessary, stop reaction by adding 100 μl of 0.2 M HCl to each well.
22. Read results on Dynatech MR7000 ELISA reader with test filter at 410 nM and reference filter at 630 nM.

Pyk2 Bioassay

This assay is used to measure the in vitro kinase activity of HA epitope-tagged full length pyk2 (FL.pyk2-HA) in an ELISA assay.

Materials and Reagents
1. Corning 96-well ELISA plates.
2. 12CA5 monoclonal anti-HA antibody (SUGEN, Inc.)
3. PBS (Dulbecco's Phosphate-Buffered Saline (Gibco Catalog #450-1300EB)
4. TBST Buffer: for 1 L, mix 8.766 g NaCl, 6.057 g TRIS and 1 ml of 0.1% Triton X-100 in approx. 900 ml dH$_2$O. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue H$_2$O.
8. 10 mM ATP in dH$_2$O.
9. 1M MnCl$_2$.
10. 1M MgCl$_2$.
11. 1M Dithiothreitol (DTT).
12. 10× Kinase buffer phosphorylation: mix 5.0 ml 1M Hepes (pH 7.5), 0.2 ml 1M MnCl$_2$, 1.0 ml 1 M MgCl$_2$, 1.0 ml 10% Triton X-100 in 2.8 ml dH$_2$O. Just prior to use, add 0.1 ml 1M DTT.
13. NUNC 96-well V bottom polypropylene plates.
14. 500 mM EDTA in dH$_2$O.
15. Antibody dilution buffer: for 100 mL, 1 mL 5% BSA/PBS and 1 mL 10% Tween-20 in 88 mL TBS.
16. HRP-conjugated anti-Ptyr (PY99, Santa Cruz Biotech Cat. No. SC-7020).
17. ABTS, Moss, Cat. No. ABST-2000.
18. 10% SDS.

Procedure
1. Coat Corning 96 well ELISA plates with 0.5 μg per well 12CA5 anti-HA antibody in 100 μl PBS. Store overnight at 4° C.
2. Remove unbound HA antibody from wells by inverting plate. Wash plate with dH$_2$O. Pat the plate on a paper towel to remove excess liquid.

3. Add 150 μl Blocking Buffer to each well. Incubate, with shaking, for 30 min at room temperature.
4. Wash plate 4× with TBS-T.
5. Dilute lysate in PBS (1.5 μg lysate/100 μl PBS).
6. Add 100 μl of diluted lysate to each well. Shake at room temperature for 1 hr.
7. Wash as in step 4.
8. Add 50 μl of 2× kinase Buffer to ELISA plate containing captured pyk2-HA.
9. Add 25 μL of 400 μM test compound in 4% DMSO to each well. For control wells use 4% DMSO alone.
10. Add 25 μL of 0.5 M EDTA to negative control wells.
11. Add 25 μl of 20 μM ATP to all wells. Incubate, with shaking, for 10 minutes.
12. Stop reaction by adding 25 μl 500 mM EDTA (pH 8.0) to all wells.
13. Wash as in step 4.
14. Add 100 μL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 μL of ABST solution to each well.
17. If necessary, stop the development reaction by adding 20 μL 10% SDS to each well.
18. Read plate on ELISA reader with test filter at 410 nM and reference filter at 630 nM.

FGFR1 Bioassay

This assay is used to measure the in vitro kinase activity of FGF1-R in an ELISA assay.

Materials and Reagents
1. Costar 96-well ELISA plates (Corning Catalog #3369).
2. Poly(Glu-Tyr) (Sigma Catalog # PO275).
3. PBS (Gibco Catalog # 450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer. Mix 500 μl 1M Hepes (GIBCO), 20 μl 5% BSA/PBS, 10 μl 100 mM sodium orthovanadate and 50 μl 5M NaCl.
8. 10 mM ATP
9. ATP/MnCl$_2$ phosphorylation mix: mix 20 μL ATP, 400 μL 1M MnCl$_2$ and 9.56 ml dH$_2$O.
10. NUNC 96-well V bottom polypropylene plates (Applied Scientific Catalog # AS-72092).
11. 0.5M EDTA.
12. 0.05% TBST Add 500 μL TWEEN to 1 liter TBS.
13. Rabbit polyclonal anti-phosphotyrosine serum (SUGEN, Inc.).
14. Goat anti-rabbit IgG peroxidase conjugate (Biosource, Catalog #ALI0404).
15. ABTS Solution.
16. ABTS/H$_2$O$_2$ solution.

Procedure
1. Coat Costar 96 well ELISA plates with 1 μg per well Poly(Glu-Tyr) in 100 μl PBS. Store overnight at 4° C.
2. Wash coated plates once with PBS.
3. Add 150 μL of 5%BSA/PBS Blocking Buffer to each well. Incubate, with shaking, for 1 hr at room temperature.
4. Wash plate 2× with PBS, then once with 50 mM Hepes. Pat plates on a paper towel to remove excess liquid and bubbles.
5. Add 25 μL of 0.4 mM test compound in 4% DMSO or 4% DMSO alone (controls) to plate.
6. Dilute purified GST-FGFR1 in Kinase Dilution Buffer (5 ng kinase/50 ul KDB/well).
7. Add 50 μL of diluted kinase to each well.
8. Start kinase reaction by adding 25 μl/well of freshly prepared ATP/Mn++ (0.4 ml 1M MnCl$_2$, 40 μL 10 mM ATP, 9.56 ml dH$_2$O), freshly prepared).
9. Stop reaction with 25 μL of 0.5M EDTA.
10. Wash plate 4× with fresh TBST.
11. Make up Antibody Dilution Buffer: For 50 ml, mix 5 ml of 5% BSA, 250 μl of 5% milk and 50 μl of 100 mM sodium vanadate, bring to final volume with 0.05% TBST.
12. Add 100 μl per well of anti-phosphotyrosine (1:10000 dilution in ADB). Incubate, with shaking for 1 hr. at room temperature.
13. Wash as in step 10.
14. Add 100 μl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 μl of ABTS/H$_2$O$_2$ solution to each well.
17. Incubate, with shaking, for 10 to 20 minutes. Remove any bubbles.
18. Read assay on Dynatech MR7000 ELISA reader: test filter at 410 nM, reference filter at 630 nM.

EGFR Bioassay

This assay is used to the in vitro kinase activity of EGFR in an ELISA assay.

Materials and Reagents
1. Corning 96-well ELISA plates.
2. SUMO1 monoclonal anti-EGFR antibody (SUGEN, Inc.).
3. PBS.
4. TBST Buffer.
5. Blocking Buffer: for 100 ml, mix 5.0 g Carnation® Instant Non-fat Milk with 100 ml of PBS.
6. A431 cell lysate (SUGEN, Inc.).
7. TBS Buffer.
8. TBS+10% DMSO: for 1 L, mix 1.514 g TRIS, 2.192 g NaCl and 25 ml DMSO; bring to 1 liter total volume with dH$_2$O.
9. ATP (Adenosine-5'-triphosphate, from Equine muscle, Sigma Cat. No. A-5394), 1.0 mM solution in dH$_2$O. This reagent should be made up immediately prior to use and kept on ice.
10. 1.0 mM MnCl$_2$.
11. ATP/MnCl$_2$ phosphorylation mix: for 10 ml, mix 300 μl of 1 mM ATP, 500 μl MnCl$_2$ and 9.2 ml dH$_2$O. Prepare just prior to use, keep on ice.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. 30% Hydrogen peroxide.
18. ABTS/H$_2$O$_2$
19. 0.2 M HCl.

Procedure

1. Coat Corning 96 well ELISA plates with 0.5 μg SUMO1 in 100 μl PBS per well, hold overnight at 4° C.
2. Remove unbound SUMO1 from wells by inverting plate to remove liquid. Wash 1× with dH$_2$O. Pat the plate on a paper towel to remove excess liquid.
3. Add 150 μl of Blocking Buffer to each well. Incubate, with shaking, for 30 min. at room temperature.
4. Wash plate 3× with deionized water, then once with TBST. Pat plate on a paper towel to remove excess liquid and bubbles.
5. Dilute lysate in PBS (7 μg lysate/100 μl PBS).
6. Add 100 μl of diluted lysate to each well. Shake at room temperature for 1 hr.
7. Wash plates as in 4, above.
8. Add 120 μl TBS to ELISA plate containing captured EGFR.
9. Dilute test compound 1:10 in TBS, place in well.
10. Add 13.5 μl diluted test compound to ELISA plate. To control wells, add 13.5 μl TBS in 10% DMSO.
11. Incubate, with shaking, for 30 minutes at room temperature.
12. Add 15 μl phosphorylation mix to all wells except negative control well. Final well volume should be approximately 150 μl with 3 gM ATP/5 mM MnCl$_2$ final concentration in each well. Incubate with shaking for 5 minutes.
13. Stop reaction by adding 16.5 μl of EDTA solution while shaking. Shake for additional 1 min.
14. Wash 4× with deionized water, 2× with TBST.
15. Add 100 μl anti-phosphotyrosine (1:3000 dilution in TBST) per well. Incubate, with shaking, for 30–45 min. at room temperature.
16. Wash as in 4, above.
17. Add 100 μl Biosource Goat anti-rabbit vgG peroxidase conjugate (1:2000 dilution in TBST) to each well. Incubate with shaking for 30 min. at room temperature.
18. Wash as in 4, above.
19. Add 100 μl of ABTS/H$_2$O$_2$ solution to each well.
20. Incubate 5 to 10 minutes with shaking. Remove any bubbles.
21. If necessary, stop reaction by adding 100 μl 0.2 M HCl per well.
22. Read assay on Dynatech MR7000 ELISA reader: test filter at 410 nM, reference filter at 630 nM.

PDGFR Bioassay

This assay is used to the in vitro kinase activity of PDGFR in an ELISA assay.

Materials and Reagents

1. Corning 96-well ELISA plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. MnCl$_2$.
11. Kinase buffer phosphorylation mix: for 10 ml, mix 250 μl 1M TRIS, 200 μl 5M NaCl, 100 μl 1M MnCl$_2$ and 50 μl 100 mM Triton X-100 in enough dH$_2$O to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. ABTS/H$_2$O$_2$.
19. 0.2 M HCl.

Procedure

1. Coat Corning 96 well ELISA plates with 0.5 μg 28D4C10 in 100 μl PBS per well, hold overnight at 4° C.
2. Remove unbound 28D4C10 from wells by inverting plate to remove liquid. Wash 1× with dH$_2$O. Pat the plate on a paper towel to remove excess liquid.
3. Add 150 μl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 μg lysate/100 μl HNTG).
6. Add 100 μl of diluted lysate to each well. Shake at room temperature for 60 min.
7. Wash plates as described in Step 4.
8. Add 80 μl working kinase buffer mix to ELISA plate containing captured PDGFR.
9. Dilute test compound 1:10 in TBS in 96-well polypropylene plates.
10. Add 10 μl diluted test compound to ELISA plate. To control wells, add 10 μl TBS+10% DMSO. Incubate with shaking for 30 minutes at room temperature.
11. Add 10 μl ATP directly to all wells except negative control well (final well volume should be approximately 100 μl with 20 μM ATP in each well.) Incubate 30 minutes with shaking.
12. Stop reaction by adding 10 μl of EDTA solution to each well.
13. Wash 4× with deionized water, twice with TBST.
14. Add 100 μl anti-phosphotyrosine (1:3000 dilution in TBST) per well. Incubate with shaking for 30–45 min. at room temperature.
15. Wash as in Step 4.
16. Add 100 μl Biosource Goat anti-rabbit IgG peroxidase conjugate (1:2000 dilution in TBST) to each well. Incubate with shaking for 30 min. at room temperature.
17. Wash as in Step 4.
18. Add 100 μl of ABTS/H$_2$O$_2$ solution to each well.
19. Incubate 10 to 30 minutes with shaking. Remove any bubbles.
20. If necessary stop reaction with the addition of 100 μl 0.2 M HCl per well.
21. Read assay on Dynatech MR7000 ELISA reader with test filter at 410 nM and reference filter at 630 nM.

Cellular HER-2 Kinase Assay

This assay is used to measure HER-2 kinase activity in whole cells in an ELISA format.

Materials and Reagents

1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081).
5. HEPES (GIBCO Catalog #15630-080).
6. Growth Media: Mix 500 ml DMEM, 55 ml heat inactivated FBS, 10 ml HEPES and 5.5 ml L-Glutamine.
7. Starve Media: Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog #25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 μL of 10 mM HCl. Add 100 uL 10 mM NaOH. Add 800 μL PBS and transfer to an Eppendorf tube, store at −20° C. until ready to use.
18. HNTG Lysis Buffer: For Stock 5× HNTG, mix 23.83 g Hepes, 43.83 g NaCl, 500 ml glycerol and 100 ml Triton X-100 and enough $dH_2O$ to make 1 L of total solution.

For 1× HNTG*, mix 2 ml 5× HNTG, 100 μL 0.1M $Na_3VO_4$, 250 μL 0.2M $Na_4P_2O_7$ and 100 μL EDTA.

19. EDTA.
20. $Na_3VO_4$: To make stock solution, mix 1.84 g $Na_3VO_4$ with 90 ml $dH_2O$. Adjust pH to 10. Boil in microwave for one minute (solution becomes clear). Cool to room temperature. Adjust pH to 10. Repeat heating/cooling cycle until pH remains at 10.
21. 200 mM $Na_4P_2O_7$.
22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat # ALI0404).
24. ABTS Solution.
25. 30% Hydrogen peroxide solution.
26. $ABTS/H_2O_2$.
27. 0.2 M HCl.

Procedure

1. Coat Corning 96 well ELISA plates with SUMO1 at 1.0 μg per well in PBS, 100 μl final volume/well. Store overnight at 4° C.
2. On day of use, remove coating buffer and wash plate 3 times with $dH_2O$ and once with TBST buffer. All washes in this assay should be done in this manner, unless otherwise specified.
3. Add 100 μL of Blocking Buffer to each well. Incubate plate, with shaking, for 30 min. at room temperature. Just prior to use, wash plate.
4. Use EGFr/HER-2 chimera/3T3-C7 cell line for this assay.
5. Choose dishes having 80–90% confluence. Collect cells by trypsinization and centrifuge at 1000 rpm at room temperature for 5 min.
6. Resuspend cells in starve medium and count with trypan blue. Viability above 90% is required. Seed cells in starve medium at a density of 2,500 cells per well, 90 μL per well, in a 96 well microtiter plate. Incubate seeded cells overnight at 37° under 5% $CO_2$.
7. Start the assay two days after seeding.
8. Test compounds are dissolved in 4% DMSO. Samples are then further diluted directly on plates with starve-DMEM. Typically, this dilution will be 1:10 or greater. All wells are then transferred to the cell plate at a further 1:10 dilution (10 μl sample and media into 90 μl of starve media). The final DMSO concentration should be 1% or lower. A standard serial dilution may also be used.
9. Incubate under 5% $CO_2$ at 37° C. for 2 hours.
10. Prepare EGF ligand by diluting stock EGF (16.5 μM) in warm DMEM to 150 nM.
11. Prepare fresh HNTG* sufficient for 100 μL per well; place on ice.
12. After 2 hour incubation with test compound, add prepared EGF ligand to cells, 50 μL per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 μL per well. Place on ice for 5 minutes. Meanwhile, remove blocking buffer from ELISA plate and wash.
15. Scrape cells from plate with a micropipettor and homogenize cell material by repeatedly aspirating and dispensing the HNTG* lysis buffer. Transfer lysate to a coated, blocked, washed ELISA plate.
16. Incubate, with shaking, at room temperature for 1 hr.
17. Remove lysate, wash. Transfer freshly diluted anti-Ptyr antibody (1:3000 in TBST) to ELISA plate, 100 μL per well.
18. Incubate, with shaking, at room temperature, for 30 min.
19. Remove anti-Ptyr antibody, wash. Transfer freshly diluted BIOSOURCE antibody to ELISA plate(1:8000 in TBST, 100 μL per well).
20. Incubate, with shaking, at room temperature for 30 min.
21. Remove BIOSOURCE antibody, wash. Transfer freshly prepared $ABTS/H_2O_2$ solution to ELISA plate, 100 μL per well.
22. Incubate, with shaking, for 5–10 minutes. Remove any bubbles.
23. Stop reaction by adding 100 μL of 0.2M HCl per well.
24. Read assay on Dynatech MR7000 ELISA reader with test filter set at 410 nM and reference filter at 630 nM.

CDK2/Cyclin A Assay

This assay is used to measure the in vitro serine/threonine kinase activity of human cdk2/cyclin A in a Scintillation Proximity Assay (SPA). Materials and Reagents.

1. Wallac 96-well polyethylene terephthalate (flexi) plates (Wallac Catalog #1450-401).
2. Amersham Redivue [$\gamma^{33}$P] ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in dH$_2$O at a concentration of 5 mg/ml.
6. 20% DMSO in dH$_2$O.
7. Kinase buffer: for 10 ml, mix 9.1 ml dH$_2$O, 0.5 ml TRIS(pH 7.4), 0.2 ml 1M MgCl$_2$, 0.2 ml 10% NP40 and 0.02 ml 1M DTT, added fresh just prior to use.
8. 10 mM ATP in dH$_2$O.
9. 1M Tris, pH adjusted to 7.4 with HCl.
10. 1M MgCl$_2$.
11. 1M DTT.
12. PBS (Gibco Catalog # 14190-144).
13. 0.5M EDTA.
14. Stop solution: For 10 ml, mix 9.25 ml PBS, 0.05 ml 10 mM ATP, 0.1 ml 0.5 M EDTA, 0.1 ml 10% Triton X-100 and 1.5 ml of 50 mg/ml SPA beads.

Procedure

1. Prepare solutions of test compounds at 4× the desired final concentration in 5% DMSO. Add 10 µL to each well. For positive and negative controls, use 10 µL 20% DMSO alone in wells.
2. Dilute the peptide substrate (deb-tide) 1:250 with dH$_2$O to give a final concentration of 0.02 mg/ml.
3. Mix 24 µL 0.1 mM ATP with 24 µCi $\gamma^{33}$P ATP and enough dH$_2$O to make 600 µL.
4. Mix diluted peptide and ATP solutions 1:1 (600 µL+600 µL per plate). Add 10 µL of this solution to each well.
5. Dilute 5 µL of cdk2/cyclin A solution into 2.1 ml 2× kinase buffer (per plate). Add 20 µL enzyme per well. For negative controls, add 20 µL 2× kinase buffer without enzyme.
6. Mix briefly on a plate shaker; incubate for 60 minutes.
7. Add 200 µL stop solution per well.
8. Let stand at least 10 min.
9. Spin plate at approx. 2300 rpm for 10–15 min.
10. Count plate on Trilux reader.

Met Transphosphorylation Assay

This assay is used to measure phosphotyrosine levels on a poly(glutamic acid:tyrosine, 4:1) substrate as a means for identifying agonists/antagonists of met transphosphorylation of the substrate.

Materials and Reagents

1. Corning 96-well ELISA plates, Corning Catalog # 25805-96.
2. Poly(glu-tyr), 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 ml PBS, filter through a 4 µm filter.
6. Purified GST fusion protein containing the Met kinase domain, SUGEN, Inc.
7. TBST Buffer.
8. 10% aqueous (MilliQue H$_2$O) DMSO.
9. 10 mM aqueous (dH$_2$O) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL dH$_2$O.
11. 4× ATP Reaction Mixture: for 10 mL, mix 0.4 mL 1 M manganese chloride and 0.02 mL 0.1 M ATP in 9.56 mL dH$_2$O.
12. 4× Negative Controls Mixture: for 10 mL, mix 0.4 mL 1 M manganese chloride in 9.6 mL dH$_2$O.
13. NUNC 96-well V bottom polypropylene plates, Applied Scientific Catalog #S-72092.
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1 M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g Na$_2$HPO$_4$ and 500 mg ABTS with sufficient dH$_2$O to make 1 L.
19. ABTS/H$_2$O$_2$: mix 15 mL ABST solution with 2 µL H$_2$O$_2$ five minutes before use.
20. 0.2 M HCl Procedure 1. Coat ELISA plates with 2 µg Poly(Glu-Tyr) in 100 µL PBS, hold overnight at 4° C.
2. Block plate with 150 µL of 5% BSA/PBS for 60 min.
3. Wash plate twice with PBS then once with 50 mM Hepes buffer pH 7.4.
4. Add 50 µl of the diluted kinase to all wells. (Purified kinase is diluted with Kinase Dilution Buffer. Final concentration should be 10 ng/well.)
5. Add 25 µL of the test compound (in 4% DMSO) or DMSO alone (4% in dH$_2$O) for controls to plate.
6. Incubate the kinase/compound mixture for 15 minutes.
7. Add 25 µL of 40 mM MnCl$_2$ to the negative control wells.
8. Add 25 µL ATP/MnCl$_2$ mixture to the all other wells (except the negative controls). Incubate for 5 min.
9. Add 25 µL 500 mM EDTA to stop reaction.
10. Wash plate 3× with TBST.
11. Add 100 µL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 µL per well and incubate at room temperature, with shaking, for one hour.
14. Wash plate 1× with PBS.
15. Add 100 µl of ABTS/H$_2$O$_2$ solution to each well.

16. If necessary, stop the development reaction with the addition of 100 µl of 0.2M HCl per well.
17. Read plate on Dynatech MR7000 ELISA reader with the test filter at 410 nM and the reference filter at 630 nM.

IGF-1 Transphosphorylation Assay

This assay is used to measure the phosphotyrosine level in poly(glutamic acid:tyrosine, 4:1) for the identification of agonists/antagonists of gst-IGF-1 transphosphorylation of a substrate.

Materials and Reagents

1. Corning 96-well ELISA plates.
2. Poly(Glu-Tyr),4:1, Sigma Cat. No. P 0275.
3. PBS, Gibco Catalog # 450-1300EB.
4. 50 mM HEPES
5. TBB Blocking Buffer: for 1 L, mix 100 g BSA, 12.1 gTRIS (pH 7.5), 58.44 g sodium chloride and 10 mL 1%TWEEN-20.
6. Purified GST fusion protein containing the IGF-1 kinase domain (SUGEN, Inc.)
7. TBST Buffer: for 1 L, mix 6.057 g Tris, 8.766 g sodium chloride and 0.5 ml TWEEN-20 with enough $dH_2O$ to make 1 liter.
8. 4% DMSO in Milli-Q $H_2O$.
9. 10 mM ATP in $dH_2O$.
10. 2× Kinase Dilution Buffer: for 100 mL, mix 10 mL 1 M HEPES (pH 7.5), 0.4 mL 5% BSA in $dH_2O$, 0.2 mL 0.1 M sodium orthovanadate and 1 mL 5 M sodium chloride with enough $dH_2O$ to make 100 mL.
11. 4× ATP Reaction Mixture: for 10 mL, mix 0.4 mL 1 M $MnCl_2$ and 0.008 mL 0.01 M ATP and 9.56 mL $dH_2O$.
12. 4× Negative Controls Mixture: mix 0.4 mL 1 M $MnCl_2$ in 9.60 mL $dH_2O$.
13. NUNC 96-well V bottom polypropylene plates.
14. 500 mM EDTA in $dH_2O$.
15. Antibody Dilution Buffer: for 100 mL, mix 10 mL 5% BSA in PBS, 0.5 mL 5% Carnation Instant Non-fat Milk in PBS and 0.1 mL 0.1 M sodium orthovanadate in 88.4 mL TBST.
16. Rabbit Polyclonal antiphosphotyrosine antibody, SUGEN, Inc.
17. Goat anti-rabbit HRP conjugated antibody, Biosource.
18. ABTS Solution.
20. $ABTS/H_2O_2$: mix 15 mL ABTS with 2 µL $H_2O_2$ 5 minutes before using.
21. 0.2 M HCl in $dH_2O$.

Procedure

1. Coat ELISA plate with 2.0 µg/well Poly(Glu, Tyr), 4:1 (Sigma P0275) in 100 µl PBS. Store plate overnight at 4° C.
2. Wash plate once with PBS.
3. Add 100 µl of TBB Blocking Buffer to each well. Incubate plate for 1 hour with shaking at room temperature.
4. Wash plate once with PBS, then twice with 50 mM Hepes buffer pH 7.5.
5. Add 25 µL of test compound in 4% DMSO (obtained by diluting a stock solution of 10 mM test compound in 100% DMSO with $dH_2O$) to plate.
6. Add 10.0 ng of gst-IGF-1 kinase in 50 µl Kinase Dilution Buffer to all wells.
7. Start kinase reaction by adding 25 µl 4× ATP Reaction Mixture to all test wells and positive control wells. Add 25 µl 4× Negative Controls Mixture to all negative control wells. Incubates for 10 minutes, with shaking, at room temperature.
8. Add 25 µl 0.5M EDTA (pH 8.0) to all wells.
9. Wash plate 4× with TBST Buffer.
10. Add rabbit polyclonal anti-phosphotyrosine antisera at a dilution of 1:10,000 in 100 µl Antibody Dilution Buffer to all wells. Incubate, with shaking, at room temperature for 1 hour.
11. Wash plate as in step 9.
12. Add 100 µL Biosource anti-rabbit HRP at a dilution of 1:10,000 in Antibody dilution buffer to all wells. Incubate, with shaking, at room temperature for 1 hour.
13. Wash plate as in step 9, follow with one wash with PBS to remove bubbles and excess Tween-20.
14. Develop by adding 100 µl/well $ABTS/H_2O_2$ to each well
15. After about 5 minutes, read on ELISA reader with test filter at 410 nm and referenced filter at 630 nm.

BrdU Incorporated Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents

1. The appropriate ligand.
2. The appropriate engineered cells.
3. BrdU Labeling Reagent: 10 mM, in PBS, pH7.4(Roche Molecular Biochemicals, Indianapolis, Ind.).
4. FixDenat: fixation solution (Roche Molecular Biochemicals, Indianapolis, Ind.).
5. Anti-BrdU-POD: mouse monoclonal antibody conjugated with peroxidase (Chemicon, Temecula, Calif.).
6. TMB Substrate Solution: tetramethylbenzidine (TMB, ready to use, Roche Molecular Biochemicals, Indianapolis, Ind.).
7. PBS Washing Solution: 1×PBS, pH 7.4.
8. Albumin, Bovine (BSA), fraction V powder (Sigma Chemical Co., USA).

General Procedure

1. Cells are seeded at 8000 cells/well in 10% CS, 2 mM Gln in DMEM, in a 96 well plate. Cells are incubated overnight at 37° C. in 5% $CO_2$.
2. After 24 hours, the cells are washed with PBS, and then are serum-starved in serum free medium (0%CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration is 10 µM) for 1.5 hours.
5. After incubation with labeling reagent, the medium is removed by decanting and tapping the inverted plate on a paper towel. FixDenat solution is added (50 µl/well) and the plates are incubated at room temperature for 45 minutes on a plate shaker.
6. The FixDenat solution is removed by decanting and tapping the inverted plate on a paper towel. Milk is added (5% dehydrated milk in PBS, 200 µl/well) as a blocking solution and the plate is incubated for 30 minutes at room temperature on a plate shaker.
7. The blocking solution is removed by decanting and the wells are washed once with PBS. Anti-BrdU-POD solution is added (1:200 dilution in PBS, 1% BSA, 50 µl/well) and the plate is incubated for 90 minutes at room temperature on a plate shaker.
8. The antibody conjugate is removed by decanting and rinsing the wells 5 times with PBS, and the plate is dried by inverting and tapping on a paper towel.
9. TMB substrate solution is added (100 µl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay
Materials and Reagents
1. Mouse EGF, 201 (Toyobo Co., Ltd., Japan).
2. 3T3/EGFRc7.
Remaining Materials and Reagents and Procedure, as Above.

EGF-Induced Her-2-driven BrdU Incorporation Assay
Materials and Reagents
1. Mouse EGF, 201 (Toyobo Co., Ltd., Japan).
2. 3T3/EGFr/Her2/EGFr (EGFr with a Her-2 kinase domain).
Remaining Materials and Reagents and Procedure, as Above.

EGF-Induced Her-4-driven BrdU Incorporation Assay
Materials and Reagents
1. Mouse EGF, 201 (Toyobo Co., Ltd., Japan).
2. 3T3/EGFr/Her4/EGFr (EGFr with a Her-4 kinase domain).
Remaining Materials and Reagents and Procedure, as Above.

PDGF-Induced BrdU Incorporation Assay
Materials and Reagents
1. Human PDGF B/B (Boehringer Mannheim, Germany).
2. 3T3/EGFRc7.
Remaining Materials and Reagents and Procedure, as Above.

FGF-Induced BrdU Incorporation Assay
Materials and Reagents
1. Human FGF2/bFGF (Gibco BRL, USA).
2. 3T3c7/EGFr
Remaining Materials and Reagents and Procedure, as Above.

IGF1-Induced BrdU Incorporation Assay
Materials and Reagents
1. Human, recombinant (G511, Promega Corp., USA)
2. 3T3/IGF1r.
Remaining Materials and Reagents and Procedure, as Above.

Insulin-Induced BrdU Incorporation Assay
Materials and Reagents
1. Insulin, crystalline, bovine, Zinc (13007, Gibco BRL, USA).
2. 3T3/H25.
Remaining Materials and Reagents and Procedure, as Above.

HGF-Induced BrdU Incorporation Assay
Materials and Reagents
1. Recombinant human HGF (Cat. No. 249-HG, R&D Systems, Inc. USA).
2. BxPC-3 cells (ATCC CRL-1687).
Remaining Materials and Reagents, as Above.
Procedure
1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 µl serum-free medium (RPMI with 0.1% BSA) for 24 hours.
3. On day 3, 25 µl containing ligand (prepared at 1 µg/ml in RPMI with 0.1% BSA; final HGF conc. is 200 ng/ml) and test compounds are added to the cells. The negative control wells receive 25 µl serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 µM, and 1:3 dilutions are used (i.e. final test compound concentration range is 0.137–100 µM).
4. After 18 hours of ligand activation, 12.5 µl of diluted BrdU labeling reagent (1:100 in RPMI, 0.1% BSA) is added to each well and the cells are incubated with BrdU (final concentration is 10 µM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 µl/well) and the plate is incubated for 90 minutes at room temperature on a plate shaker.
8. Same as General Procedure.
9. Same as General Procedure.
10. Same as General Procedure.

Exponential BrdU Incorporation Assay
This assay is used to measure the proliferation (DNA synthesis) of exponentially growing A431 cells. The assay will screen for compounds that inhibit cell cycle progression.
Materials and Reagents
Healthy growing A431 cells. The remainder of the Materials and Reagents are the same as listed above in the general protocol section.
Procedure
1. A431 cells are seeded at 8000 cells/well in 10% FBS, 2mM Gln in DMEM, on a 96-well plate. Cells are incubated overnight at 37° C. in 5% $CO_2$.
2. On day 2, test compounds are serially diluted to 7 test concentrations in the same growth medium on a 96-well plate and then are added to the cells on a 96-well tissue culture plate.
3. After 20–24 hours of incubation, diluted BrdU labeling reagent (1:100 in DMEM, 0.1% BSA) is added and the cells are incubated with BrdU (final concentration is 10 µM) for 2 hours.

Steps 5–10 of the General Procedure are used to complete the assay.

ZenSrc Assay

This assay is used to screen for inhibitors of the tyrosine kinase Src.

Materials and Reagents

1. Coating buffer: PBS containing sodium azide (0.2 mg/ml).
2. 1% w/v BSA in PBS.
3. Wash buffer: PBS containing 0.05% v/v Tween 20 (PBS-TWEEN)
4. 500 mM HEPES pH7.4.
5. ATP (40 $\mu$M)+MgCl, (80 mM) in distilled water.
6. $MgCl_2$ (80 mM) in distilled water (for no ATP blanks).
7. Test compounds, 10 mM in DMSO.
8. Assay Buffer: 100 mM HEPES, pH 7.4, containing 2 mM DTT, 0.2 mM sodium orthovanadate and 0.2 mgs/ml BSA.
9. Partially purified recombinant human Src (UBI (14-117)
10. Anti-phosphotyrosine (SUGEN rabbit polyclonal anti-PY).
11. HRP-linked goat anti-rabbit Ig (Biosource International #6430)
12. HRP substrate ABTS or Pierce Peroxidase substrate.
13. Corning ELISA plates.

Procedure

1. Coat plates with 100 $\mu$l of 20 $\mu$g/ml poly(Glu-Tyr) (Sigma Cat. No.P0275) containing 0.01% sodium azide. Hold overnight at 4° C.
2. Block with 1% BSA at 100 $\mu$l/well for one hour at room temperature.
3. Plate test compounds (10 mM in DMSO) at 2ul/well on a Costar plate ready for dilution with $dH_2O$ and plating to reaction plates.
4. Dilute Src kinase 1:10,000 in Reaction Buffer, for 5 plates prepare 25 ml as follows: 2.5 mls 1M HEPES pH7.4 (stored sterile at 4° C.), 21.85 ml distilled water, 0.1 ml 5% BSA, 0.5 ml 10 mM sodium orthovanadate (stored sterile at 4° C.), 50 $\mu$l 1.0M DTT (stored frozen at −20° C.), and 2.5 $\mu$l Src Kinase (stored frozen at −80° C.).
5. Add 48 $\mu$l of distilled water to the 2 $\mu$l of each compound in the dilution plate then add 25 $\mu$l/well of this to the reaction plate.
6. Add 50 $\mu$l of HRP to each reaction buffer well and then 25 $\mu$l ATP-$MgCl_2$/well ($MgCl_2$ only to no ATP blanks). Incubate at room temperature for 15 minutes on plate shaker. Stop reaction by adding 25 $\mu$l of 0.5M EDTA to each well.
7. Wash 4× with PBS-TWEEN.
8. Add 100 $\mu$l anti-phosphotyrosine (1:10,000 of anti-pTyr serum or 1:3,000 of 10% glycerol diluted PA-affinity purified antibody) in PBS-TWEEN containing 0.5% BSA, 0.025% Non-fat milk powder and 100 $\mu$M sodium orthovanadate. Incubate with continuous shaking at room temperature for one hour.
9. Wash plates 4× with PBS-TWEEN.
10. Add 100 $\mu$l HRP-linked Ig (1:5,000) in PBS-TWEEN containing 0.5% BSA, 0.025% Non-fat milk powder, 100 $\mu$M sodium orthovanadate. Incubate with shaking at room temperature for one hour.
11. Wash plates 4× with PBS-TWEEN and then once with PBS.
12. Develop plate using ABTS or other peroxidase substrate.

Cell Cycle Analysis

A431 cells in standard growth medium are exposed to a desired concentration of a test compound for 20–24 hours at 37° C. The cells are then collected, suspended in PBS, fixed with 70% ice-cold methanol and stained with propidium iodide. The DNA content is then measured using a FACScan flow cytometer. Cell cycle phase distribution can then be estimated using CellFIT software (Becton-Dickinson).

HUV-EC-C Assay

This assay is used to measure a compound's activity against PDGF-R, FGF-R, VEGF, aFGF or Flk-1/KDR, all of which are naturally expressed by HUV-EC cells.

DAY 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 $cm^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).

2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8–1.0×$10^5$ cells/ml.

3. Add cells to 96-well flat-bottom plates at 100 $\mu$l/well or 0.8–1.0×$10^4$ cells/well, incubate ~24 h at 37° C., 5% $CO_2$.

DAY 1

1. Make up two-fold test compound titrations in separate 96-well plates, generally 50 $\mu$M on down to 0 $\mu$M. Use the same assay medium as mentioned in day 0, step 2 above. Titrations are made by adding 90 $\mu$l/well of test compound at 200 $\mu$M (4× the final well concentration) to the top well of a particular plate column. Since the stock test compound is usually 20 mM in DMSO, the 200 $\mu$M drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 $\mu$l/well. Take 60 $\mu$l from the 120 $\mu$l of 200 $\mu$M test compound dilution in the top well of the column and mix with the 60 $\mu$l in the second well of the column. Take 60 $\mu$l from this well and mix with the 60 $\mu$l in the third well of the column, and so on until two-fold titrations are completed. When the next-to-the-last well is mixed, take 60 $\mu$l of the 120 $\mu$l in this well and discard it. Leave the last well with 60 $\mu$l of DMSO/media diluent as a non-test compound-containing control. Make 9 columns of titrated test compound, enough for triplicate wells each for: (1) VEGF (obtained from Pepro Tech Inc., catalogue no.

100–200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 µl/well of the test compound dilutions to the 96-well assay plates containing the $0.8–1.0\times10^4$ cells/100 µl/well of the HUV-EC-C cells from day 0 and incubate ~2 h at 37° C., 5% $CO_2$.

3. In triplicate, add 50 µl/well of 80 µg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 µl test compound dilution, 50 µl growth factor or media, and 100 µl cells, which calculates to 200 µl/well total. Thus the 4× concentrations of test compound and growth factors become 1× once everything has been added to the wells.

DAY 2

1. Add $^3$H-thymidine (Amersham, catalogue no. TRK-686) at 1 µCi/well (10 µl/well of 100 µCi/ml solution made up in RPMI media+10% heat-inactivated fetal bovine serum) and incubate 24 h at 37° C., 5% $CO_2$. RPMI is obtained from Gibco BRL, catalogue no. 11875-051.

DAY 3

1. Freeze plates overnight at –20° C.

DAY 4

Thaw plates and harvest with a 96-well plate harvester (Tomtec Harvester 96®) onto filter mats (Wallac, catalogue no. 1205-401), read counts on a Wallac Betaplate™ liquid scintillation counter.

Vascular Permeability Assay

Increased vascular permeability in tumor-dependent angiogenesis is due to a loosening of gap junctions in response to vascular endothelial growth factor (VEGF). The Miles assay for vascular permeability (Miles and Miles, *J. Physiol.* 118: 228–257 (1952)) has been adapted to athymic mice in order to evaluate the ability of the compounds of the present invention to inhibit VEGF-induced vascular permeability in vivo.

General Procedure

Test compound or vehicle is administered prior to (typically it is 4 hours prior) to VEGF injection. 100 µl of 0.5% Evan's blue dye in PBS is injected intravenously via lateral tail vein injections using a 27 gauge needle. Sixty minutes later, animals are anesthetized using the inhalant Isofluorane. Following anesthesia, VEGF (100 ng of VEGF in 20 µl of PBS) is injected intradermally in two spots and PBS (20 µl) is injected in two spots in a grid pattern in the back of each animal. At a designated timepoint of up to 1 hour after VEGF injection, the animals are euthanized by $CO_2$ and the skin patches are dissected and photographed. Based on a published report (Alicieri et al., *Mol. Cell* 4: 915–914 (1999)) quantitative evaluation of the VEGF-dependent dye leakage into mouse skin can be achieved following elution of the dye from skin patches.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Poylsen, 1969, Acta Pathol. Microbial. Scand. 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject 10$^7$ tumor cells in a volume of 100 µl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Additional Assays

Additional assays which may be used to evaluate the compounds of this invention include, without limitation, a bio-flk-1 assay, an EGF receptor-HER2 chimeric receptor assay in whole cells, a bio-src assay, a bio-lck assay and an assay measuring the phosphorylation function of raf. The protocols for each of these assays may be found in U.S. application Ser. No. 09/099,842, which is incorporated by reference, including any drawings, herein. Additionally, U.S. Pat. No. 5,792,783, filed Jun. 5, 1996 and U.S. application Ser. No. 09/322,297, filed May 28, 1999 are incorporated by reference as if fully set forth herein.

Plasma Stability Test

The prodrug (3Z)-3-[(3,5-dimethyl-1H-pyrrol-2-yl)-methylidene]-1-(1-pyrrolidinylmethyl)-1,3-dihydro-2H-indol-2-one was administered IV at 2 mg/mL to dogs. Levels of both prodrug and drug (3(Z)-3-[(3,5-dimethyl-1H-pyrrol-2-yl)-methylidene]-1,3-dihydro-2H-indol-2-one) were followed by HPLC analysis of blood plasma for 4 hours following dosing. This study showed that the half-life for conversion of the prodrug to drug was 7.3 min. From a plot of drug concentration vs. time, the area under the curve indicated that 80% of the prodrug was converted into drug.

Formulation Examples

The formulations being evaluated are listed in Tables 1 and 2 and are described below:

[A] Solid Formulations to be Reconstituted to a Stable Infusate (Table 1)

(1) Lyophilized Formulation:

(a) Captisol Based: This formulation uses Captisol and an acidic agent to form an in situ salt at a pH of 1.5–2.0 to compound and lyophilize solutions of drug at concentrations of 20.0–25.0 mg/mL. The lyophilized cake is reconstituted with an IV fluid to provide a stable infusate at 2 mg/mL or higher at pH 3.

(b) Non-Captisol based: This formulation uses small amounts of a surfactant such as Polysorbate-80 or Cremophor EL and an acidic agent to form an in-situ salt at a pH of 1.5–2.0 to compound and lyophilize solutions of drug at concentrations of 20.0–25.0 mg/mL. The lyophilized cake is reconstituted with cosolvent-surfactant based aqueous diluent such as PEG-300-Polysorbate 80 or PEG-300-Cremophor EL to provide a stable infusate at 2 mg/mL or higher at pH 3.

(2) Sterile API fill:

The drug is filled as a sterile powder fill in a container and will be reconstituted with a specific co-solvent—surfactant based aqueous diluent to provide a stable infusate at 2 mg/mL or higher of drug at pH 3.

[B] Solution Concentrate to be Diluted to a Stable Infusate (Table 2)

The drug is solubilized in a non-aqueous mixture of co-solvents and surfactants at a high concentration such that it can be diluted with aqueous diluents to a stable infusate. The concentration of the drug in the infusate is at a concentration of 2 mg/mL or higher, at pH 3. The total levels of the co-solvent is less than 15% and the levels of surfactant is than 0.5%.

TABLE 1

| Formulation Attributes | (1) Solid formulations | | | | | |
|---|---|---|---|---|---|---|
| | Lyophilized - Captisol based | | Lyophilized Non-Captisol based | | Sterile API Fill | |
| Dose/50 CC vial (mgs) | 200–300 | | 200–300 | | 300–400 | |
| Sterile API fill in vial | NA | | NA | | 300–400 mg | |
| Composition - Lyophilized Cake | drug (mg) | 200–300 | drug (mg) | 200–300 | NA | |
| | Acid (M) | 1.4 | Acid (M) | 1.4 | | |
| | Antioxidant (mg) | 0–10 | Antioxidant (mg) | 0–10 | | |
| | Captisol (mg) | 2000–3000 | Filler (mg) | 200–300 | | |
| | | | Polysorbate-80 (mg) | 0–50 | | |
| Composition - Reconstitution Fluid | 0.9% NaCl, D5W, | | PEG-300 (% w/v) | 5–20 | PEG-300 (% w/v) | 5–20 |
| | | | Polysorbate-80 (% w/v) | 0–1.0 | Polysorbate-80 (% w/v) | 0–1.0 |
| | | | Citrate Buffer pH 3.0 0.1M (% w/v) | 30–40 | Citrate Buffer pH 3.0 0.1M (% w/v) | 30–40 |
| | | | Water | (qs to volume) | Water | (qs to volume) |
| Composition - Reconstituted Infusate (Administered to Patient) | drug (mg/mL) | 2–3 | drug (mg/mL) | 2–3 | drug (mg/mL) | 2–3 |
| | Acid (Molar) | 1.4 | Acid (Molar) | 1.4 | Acid (Molar) | 1.4 |
| | Antioxidant (mg/mL) | 0–1.0 | Antioxidant (mgmL) | 0–1.0 | Antioxidant (mg/mL) | 0–1.0 |
| | Captisol (mg/mL) | 20–30 | Filler (mg/mL) | 2–3 | Filler (mg/mL) | 2–3 |
| | IV fluid | (qs to volume) | PEG-300 (mg/mL) | 50–200 | PEG-300 (mg/mL) | 50–200 |
| | pH | 3.0 | Polysorbate-80 (mg/mL) | 0–10 | Polysorbate-80 (mg/mL) | 0–10 |
| | | | Citrate Buffer 0.1M, pH 3.0 (mL) | 0.3 | Citrate Buffer 0.1M, pH 3.0 (mL) | 0.3 |
| | | | Water | (qs to volume) | Water | (qs to volume) |
| | | | pH | 3.0 | pH | 3.0 |
| Composition - Prelyophilate | drug (mg/mL) | 20–30 | drug (mg/mL) | 20–30 | NA | |
| | Acid (Molar) | 1.4 | Acid (Molar) | 1.4 | | |
| | Antioxidant (mg/mL) | 0–10 | Antioxidant (mg/mL) | 0–10 | | |
| | Captisol (mg/mL) | 200–300 | | | | |

TABLE 1-continued

| Formulation | (1) Solid formulations | | | |
|---|---|---|---|---|
| Attributes | Lyophilized - Captisol based | | Lyophilized Non-Captisol based | Sterile API Fill |
| | Water for Injection | qs to 1.0 mL | Filler (mg/mL) 20–30 | |
| | pH | 1.5–2.0 | Polysorbate-80 (mg) 0–50 | |
| | | | Water for Injection qs to 1.0 mL | |
| | | | pH 1.5–2.0 | |

Acids used: Methane sulfonic acid, Tartaric acid, Citric acid, succinic acid is used in a 1:1.4 molar ratio for in situ salt formation
Cosolvents- PEG-300, PEG-400
Surfactants: Polysorbate-80, Cremophor EL
Captisol ®: Sulfobutylether Cyclodextrin
Drug: Compound of Example 2

TABLE 2

Composition of Solution Formulation

| Ingredients | Composition (% w/v) or mg/mL |
|---|---|
| Drug | 1.2–2.5 (12–25 mg/mL) |
| Cosolvent - (PEG-300, PEG-400) | 70–90 |
| Surfactant | 0–10 |
| Dimethylacetamide | 0–2 |
| Salt forming agent (Methane sulfonic acid, Tartaric acid, Citric Acid, Succinic Acid) | Equivalent to 1.4 M ratio of the API |
| Alcohol | Qs to Volume |

Formulation to be diluted 10 fold with pharmaceutically acceptable IV fluids.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

What is claimed is:

1. A compound of the formula III:

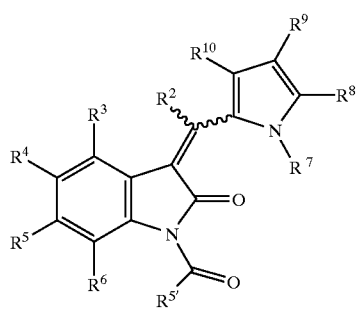

III wherein:
$R^2$ is hydrogen;
$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —$NR^{11}R^{12}$ where $R^{11}$ and $R^{12}$ are independently selected from the group consisting of hydrogen, alkyl, cycloalkyl, aryl, carbonyl, acetyl, sulfonyl, and trifluoromethanesulfonyl or $R^{11}$ and $R^{12}$ together with the nitrogen atom to which they are attached combine to form a five- or six-membered heteroalicyclic ring provided that at least two of $R^3$, $R^4$, $R^5$ and $R^6$ are hydrogen; or $R^3$ and $R^4$, $R^4$ and $R^5$, or $R^5$ and $R^6$ combine to form a six-membered aryl ring, a methylenedioxy or an ethylenedioxy group;

$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl;

$R^8$, $R^9$ and $R^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfmyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino, -(alk$_1$)Z (where alk$_1$ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —$NR^{11}R^{12}$ wherein $R^{11}$ and $R^{12}$ are as defined above;

$R^{5'}$ is alkyl; or a pharmaceutically acceptable salt thereof.

2. A compound of the formula III:

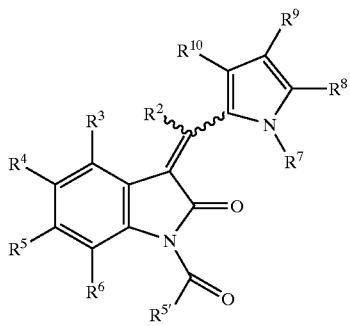

wherein:
R² is hydrogen;
R³, R⁴, R⁵ and R⁶ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR¹¹R¹² where R¹¹ and R¹² are independently selected from the group consisting of hydrogen, alkyl, cycloalkyl, aryl, carbonyl, acetyl, sulfonyl, and trifluoromethanesulfonyl, or R¹¹ and R¹², together with the nitrogen atom to which they are attached, combine to form a five- or six-membered heteroalicyclic ring provided that at least two of R³, R⁴, R⁵ and R⁶ are hydrogen; or
R³ and R⁴, R⁴ and R⁵, or R⁵ and R⁶ combine to form a six-membered aryl ring, a methylenedioxy or an ethylenedioxy group;
R⁷ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl;
R⁸, R⁹ and R¹⁰ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonarnido, carbonyl, C-carboxy, O-carboxy, cyano, nitro, halo, O-carbamyl, N-carbamyl, O-thiocarbamyl, N-thiocarbamyl, C-amido, N-amido, amino, -(alk₁)Z (where alk₁ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl) and —NR¹¹R¹² wherein R¹¹ and R¹² are as defined above; and
R⁵' is alkyl; or
a pharmaceutically acceptable salt thereof.

3. The compound of claim 2, wherein R⁵' is alkyl substituted with C-carboxy, —NR¹¹R¹² or ammonium.

4. The compound of claim 3, wherein:
R³ is hydrogen or lower unsubstituted alkyl;
R⁴ is selected from the group consisting of hydrogen, halogen, aryl and S-sulfonamido;
R⁵ is selected from the group consisting of hydrogen, lower alkyl, lower alkoxy, aryl, and heteroaryl; and R⁶ is hydrogen.

5. The compound of claim 3, wherein:
R³ is hydrogen;
R⁴ is selected from the group consisting of hydrogen, chloro, fluoro, bromo and phenyl;
R⁵ is selected from the group consisting of hydrogen, methyl, ethyl, methoxy, phenyl, and pyridyl.

6. The compound of claim 3, wherein:
R³, R⁴, R⁵ and R⁶ are hydrogen; and
R⁸ and R¹⁰ are unsubstituted lower alkyl; and
R⁹ is hydrogen, C-amido, or -(alk₁)Z (where alk₁ is selected from the group consisting of alkyl, alkenyl or alkynyl and Z is hydroxy, alkoxy, carboxy, nitro, cyano, amino, guanidino, amido, ureido, sulfonamido, sulfinyl, sulfonyl, phosphonate, morpholino, piperazinyl or tetrazolyl).

7. The compound of claim 3, wherein the compound is:

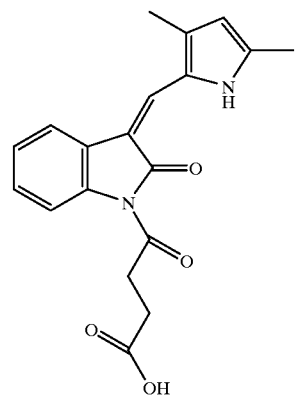

8. The compound of claim 3, wherein the compound is selected from the group consisting of:

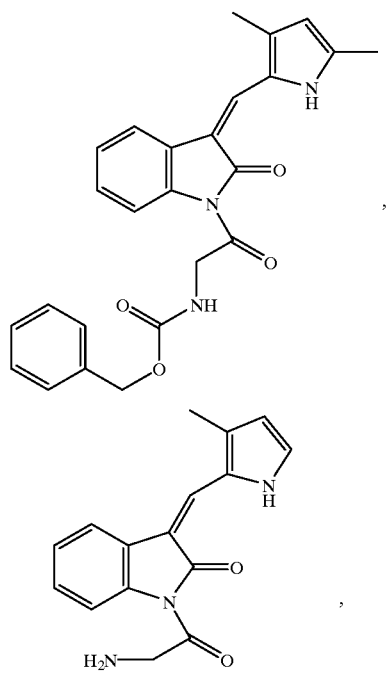

-continued

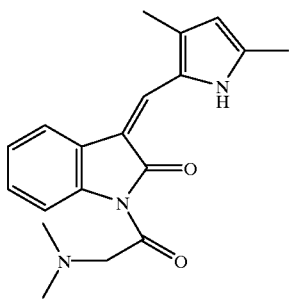

and

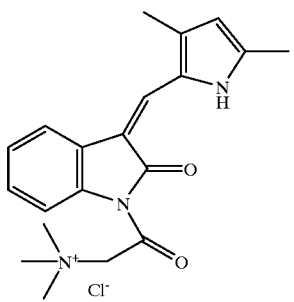

9. A pharmaceutical composition comprising a compound of claim 1 and a pharmaceutically acceptable carrier.

10. A pharmaceutical composition comprising a compound of any one of claims 2–8 and a pharmaceutically acceptable carrier.

11. The pharmaceutical composition of claim 1, wherein said composition is administered orally.

12. The pharmaceutical composition of claim 1, wherein said composition is administered parenterally.

13. A method for treating diseases related to unregulated protein kinase signal transduction comprising administering to a subject in need thereof a therapeutically effective amount of a compound of claim 1.

14. The method of claim 13 or 39, wherein said disease is selected from the group consisting of cancer, blood vessel proliferative disorders, fibrotic disorders, mesangial cell proliferative disorders, metabolic diseases and infectious diseases.

15. The method of claim 14, wherein the cancer is selected from the group consisting of colorectal cancer, Kaposi's sarcoma and lung cancer.

16. The method of claim 14, wherein the blood vessel proliferative disorder is selected from the group consisting of arthritis and restenosis.

17. The method of claim 14, wherein the fibrotic disorder is selected from the group consisting of hepatic cirrhosis and atherosclerosis.

18. The method of claim 14, wherein the mesangial cell proliferative disorder is selected from the group consisting of glomerulonephritis, diabetic nephropathy, malignant nephrosclerosis, thrombotic microangiopathy syndromes, transplant rejection and glomerulopathies.

19. The method of claim 14, wherein the metabolic disease is selected from the group consisting of psoriasis, diabetes mellitus, wound healing, inflammation and neurodegenerative diseases.

* * * * *

UNITED STATES PATENT AND TRADEMARK OFFICE
CERTIFICATE OF CORRECTION

PATENT NO. : 6,482,848 B2
DATED : November 19, 2002
INVENTOR(S) : Malcolm Wilson Moon et al.

It is certified that error appears in the above-identified patent and that said Letters Patent is hereby corrected as shown below:

Title page,
Item [73], Assignee, should read as follows:
-- [73]  Assignee(s):  Sugen, Incorporated, South San Francisco, CA (US) and
Pharmacia & Upjohn Company, Kalamazoo, MI (US) --

Signed and Sealed this

Twenty-sixth Day of October, 2004

JON W. DUDAS
*Director of the United States Patent and Trademark Office*